US012758778B2

(12) United States Patent
Dinsmoor et al.

(10) Patent No.: US 12,758,778 B2
(45) Date of Patent: Oct. 13, 2026

(54) LOCAL FIELD POTENTIAL (LFP) SENSING FOR NEUROSTIMULATION CONTROL

(71) Applicant: Medtronic, Inc., Minneapolis, MN (US)

(72) Inventors: David A. Dinsmoor, North Oaks, MN (US); Leonid M. Litvak, Bet Shemesh (IL); Juan G. Hincapie, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 370 days.

(21) Appl. No.: 18/547,191

(22) PCT Filed: Feb. 10, 2022

(86) PCT No.: PCT/US2022/070617

§ 371 (c)(1),
(2) Date: Aug. 21, 2023

(87) PCT Pub. No.: WO2022/183163

PCT Pub. Date: Sep. 1, 2022

(65) Prior Publication Data

US 2024/0123235 A1 Apr. 18, 2024

Related U.S. Application Data

(60) Provisional application No. 63/238,290, filed on Aug. 30, 2021, provisional application No. 63/153,278, filed on Feb. 24, 2021.

(51) Int. Cl.

| | |
|---|---|
| ***A61N 1/36*** | (2006.01) |
| ***A61B 5/388*** | (2021.01) |
| ***A61N 1/372*** | (2006.01) |

(52) U.S. Cl.
CPC .......... *A61N 1/36139* (2013.01); *A61B 5/388* (2021.01); *A61N 1/36062* (2017.08); *A61N 1/37235* (2013.01)

(58) Field of Classification Search
CPC ............ A61N 1/36139; A61N 1/36062; A61N 1/37235; A61N 1/36067; A61N 1/36071;
(Continued)

(56) References Cited

U.S. PATENT DOCUMENTS

| | | | |
|---|---|---|---|
| 5,603,726 | A | 2/1997 | Schulman et al. |
| 5,800,465 | A | 9/1998 | Thompson et al. |

(Continued)

FOREIGN PATENT DOCUMENTS

| | | | |
|---|---|---|---|
| EP | 2396072 | B1 | 3/2013 |
| EP | 3013413 | A1 | 5/2016 |

(Continued)

OTHER PUBLICATIONS

M. Fabietti et al., "Neural Network-based Artifact Detection in Local Field Potentials Recorded from Chronically Implanted Neural Probes," 2020 International Joint Conference on Neural Networks (IJCNN), Glasgow, UK, 2020, pp. 1-8, doi: 10.1109/IJCNN48605.2020.9207320 (Year: 2020).*

(Continued)

*Primary Examiner* — Niketa Patel
*Assistant Examiner* — Attiya Sayyada Hussaini
(74) *Attorney, Agent, or Firm* — Shumaker & Sieffert, P.A.

(57) ABSTRACT

A system may be configured to sense local field potentials (LFPs) from electrodes placed in epidural space near the spine of a patient. The system may be configured to analyze the sensed LFPs and determine a change in a state of the patient, such as a physiological state of the patient. The system may use such analysis to update and/or suggest (Continued)

parameters for delivery of electrical stimulation therapy. The system may further be configured to analyze LFPs in a frequency domain by applying a wavelet transform or other transform to sensed LFPs.

21 Claims, 11 Drawing Sheets

(58) Field of Classification Search
CPC ....... A61B 5/388; A61B 5/407; A61B 5/4824; A61B 5/6877; A61B 5/7217; A61B 5/726; A61B 5/686
See application file for complete search history.

(56) References Cited

U.S. PATENT DOCUMENTS

| | | | |
|---|---|---|---|
| 6,157,861 | A | 12/2000 | Faltys et al. |
| 6,205,360 | B1 | 3/2001 | Carter |
| 6,289,247 | B1 | 9/2001 | Faltys et al. |
| 6,314,325 | B1 | 11/2001 | Fitz |
| 6,421,566 | B1 | 7/2002 | Holsheimer |
| 6,505,078 | B1 | 1/2003 | King et al. |
| 6,675,046 | B2 | 1/2004 | Holsheimer |
| 6,850,802 | B2 | 2/2005 | Holsheimer |
| 6,988,006 | B2 | 1/2006 | King et al. |
| 7,076,292 | B2 | 7/2006 | Forsberg |
| 7,206,640 | B1 | 4/2007 | Overstreet |
| 7,333,858 | B2 | 2/2008 | Killian et al. |
| 7,577,480 | B2 | 8/2009 | Zeijlemaker |
| 7,616,999 | B2 | 11/2009 | Overstreet et al. |
| 7,657,318 | B2 | 2/2010 | King et al. |
| 7,689,289 | B2 | 3/2010 | King |
| 7,742,810 | B2 | 6/2010 | Moffitt et al. |
| 7,792,583 | B2 | 9/2010 | Miesel et al. |
| 8,036,747 | B2 | 10/2011 | Thacker et al. |
| 8,090,446 | B2 | 1/2012 | Fowler et al. |
| 8,504,150 | B2 | 8/2013 | Skelton |
| 8,620,441 | B2 | 12/2013 | Greenberg et al. |
| 8,676,329 | B2 | 3/2014 | Wacnik et al. |
| 8,694,108 | B2 | 4/2014 | Alataris et al. |
| 8,708,934 | B2 | 4/2014 | Skelton et al. |
| 8,712,533 | B2 | 4/2014 | Alataris et al. |
| 8,712,534 | B2 | 4/2014 | Wei |
| 8,751,009 | B2 | 6/2014 | Wacnik |
| 8,897,888 | B2 | 11/2014 | Parker et al. |
| 8,923,984 | B2 | 12/2014 | Parker et al. |
| 9,002,460 | B2 | 4/2015 | Parker |
| 9,072,910 | B2 | 7/2015 | Parker et al. |
| 9,089,714 | B2 | 7/2015 | Robinson |
| 9,089,715 | B2 | 7/2015 | Parker et al. |
| 9,138,582 | B2 | 9/2015 | Doan et al. |
| 9,155,892 | B2 | 10/2015 | Parker et al. |
| 9,283,373 | B2 | 3/2016 | Parker et al. |
| 9,302,112 | B2 | 4/2016 | Bornzin et al. |
| 9,339,655 | B2 | 5/2016 | Carbunaru |
| 9,364,667 | B1 | 6/2016 | Dinsmoor et al. |
| 9,381,356 | B2 | 7/2016 | Parker et al. |
| 9,386,934 | B2 | 7/2016 | Parker et al. |
| 9,387,325 | B1 | 7/2016 | Min et al. |
| 9,566,439 | B2 | 2/2017 | Single et al. |
| 9,597,507 | B2 | 3/2017 | Johanek et al. |
| 9,700,713 | B2 | 7/2017 | Robinson et al. |
| 9,872,990 | B2 | 1/2018 | Parker et al. |
| 9,993,646 | B2 | 6/2018 | Parramon et al. |
| 10,183,168 | B2 | 1/2019 | Baru et al. |
| 10,569,088 | B2 | 2/2020 | Dinsmoor et al. |
| 10,835,170 | B2 | 11/2020 | Saab |
| 10,933,242 | B2 | 3/2021 | Torgerson |
| 11,129,989 | B2 | 9/2021 | Dinsmoor et al. |
| 11,129,991 | B2 | 9/2021 | Dinsmoor et al. |
| 2004/0267333 | A1 | 12/2004 | Kronberg |
| 2008/0221640 | A1 | 9/2008 | Overstreet et al. |
| 2008/0300655 | A1 | 12/2008 | Cholette |
| 2011/0054570 | A1 | 3/2011 | Lane |
| 2011/0071589 | A1 | 3/2011 | Starkebaum et al. |
| 2011/0077712 | A1 | 3/2011 | Killian |
| 2011/0125223 | A1 | 5/2011 | Carbunaru et al. |
| 2011/0251583 | A1 | 10/2011 | Miyazawa et al. |
| 2012/0155188 | A1 | 6/2012 | Buettner et al. |
| 2013/0208390 | A1 | 8/2013 | Singh et al. |
| 2013/0268021 | A1 | 10/2013 | Moffitt |
| 2013/0289664 | A1 | 10/2013 | Johanek |
| 2013/0289683 | A1 | 10/2013 | Parker et al. |
| 2014/0005753 | A1 | 1/2014 | Carbunaru |
| 2014/0025146 | A1 | 1/2014 | Alataris et al. |
| 2014/0031896 | A1 | 1/2014 | Alataris et al. |
| 2014/0031905 | A1 | 1/2014 | Irazoqui et al. |
| 2014/0074189 | A1 | 3/2014 | Moffitt |
| 2014/0142656 | A1 | 5/2014 | Alataris et al. |
| 2014/0142673 | A1 | 5/2014 | Alataris et al. |
| 2014/0194772 | A1 | 7/2014 | Single et al. |
| 2014/0236042 | A1 | 8/2014 | Parker et al. |
| 2014/0236257 | A1 | 8/2014 | Parker et al. |
| 2014/0243924 | A1 | 8/2014 | Zhu et al. |
| 2014/0243926 | A1 | 8/2014 | Carcieri et al. |
| 2014/0243931 | A1 | 8/2014 | Parker et al. |
| 2014/0277282 | A1 | 9/2014 | Jaax |
| 2014/0288577 | A1 | 9/2014 | Robinson et al. |
| 2014/0293737 | A1 | 10/2014 | Parker et al. |
| 2014/0296936 | A1 | 10/2014 | Alataris et al. |
| 2014/0324143 | A1 | 10/2014 | Robinson et al. |
| 2014/0358024 | A1* | 12/2014 | Nelson ................ A61B 5/4833 607/45 |
| 2014/0371813 | A1 | 12/2014 | King et al. |
| 2014/0378941 | A1 | 12/2014 | Su et al. |
| 2014/0379043 | A1 | 12/2014 | Howard |
| 2015/0005842 | A1 | 1/2015 | Lee et al. |
| 2015/0012068 | A1 | 1/2015 | Bradley et al. |
| 2015/0032181 | A1 | 1/2015 | Baynham et al. |
| 2015/0039057 | A1 | 2/2015 | Della Santina et al. |
| 2015/0057729 | A1 | 2/2015 | Parker et al. |
| 2015/0127062 | A1 | 5/2015 | Holley |
| 2015/0179177 | A1 | 6/2015 | Nagao |
| 2015/0282725 | A1 | 10/2015 | Single |
| 2015/0313487 | A1 | 11/2015 | Single et al. |
| 2015/0360031 | A1 | 12/2015 | Bornzin et al. |
| 2015/0374999 | A1 | 12/2015 | Parker et al. |
| 2016/0082252 | A1 | 3/2016 | Hershey et al. |
| 2016/0121124 | A1 | 5/2016 | Johanek et al. |
| 2016/0129272 | A1 | 5/2016 | Hou et al. |
| 2016/0136420 | A1 | 5/2016 | Brink et al. |
| 2016/0157769 | A1 | 6/2016 | Min et al. |
| 2016/0158550 | A1 | 6/2016 | Hou et al. |
| 2016/0158551 | A1 | 6/2016 | Kent et al. |
| 2016/0166164 | A1 | 6/2016 | Obradovic et al. |
| 2016/0175594 | A1* | 6/2016 | Min .................. A61N 1/36171 607/72 |
| 2016/0206883 | A1 | 7/2016 | Bornzin et al. |
| 2016/0287126 | A1 | 10/2016 | Parker et al. |
| 2016/0287182 | A1 | 10/2016 | Single |
| 2016/0346534 | A1 | 12/2016 | Isaacson et al. |
| 2016/0361542 | A1 | 12/2016 | Kaula et al. |
| 2017/0001017 | A9 | 1/2017 | Parker et al. |
| 2017/0049345 | A1 | 2/2017 | Single |
| 2017/0071490 | A1 | 3/2017 | Parker et al. |
| 2017/0135624 | A1 | 5/2017 | Parker |
| 2017/0173332 | A1 | 6/2017 | Overstreet |
| 2017/0209695 | A1 | 7/2017 | Solomon |
| 2017/0216587 | A1 | 8/2017 | Parker |
| 2017/0216602 | A1 | 8/2017 | Waataja et al. |
| 2017/0296823 | A1 | 10/2017 | Hershey et al. |
| 2017/0361101 | A1 | 12/2017 | Single |
| 2017/0361103 | A1 | 12/2017 | Hadjiyski |
| 2018/0056073 | A1 | 3/2018 | Torgerson |
| 2018/0071530 | A1* | 3/2018 | Giftakis ............... A61N 1/3614 |
| 2018/0078769 | A1 | 3/2018 | Dinsmoor et al. |
| 2018/0110987 | A1 | 4/2018 | Parker |
| 2018/0117335 | A1 | 5/2018 | Parker et al. |
| 2018/0126169 | A1 | 5/2018 | Hou et al. |
| 2018/0132760 | A1 | 5/2018 | Parker |
| 2018/0154144 | A1 | 6/2018 | Brink et al. |
| 2018/0193650 | A1* | 7/2018 | Srivastava ......... A61B 5/02416 |
| 2018/0200520 | A1 | 7/2018 | Tranchina et al. |

(56) References Cited

U.S. PATENT DOCUMENTS

2018/0228421 A1* 8/2018 Saab .................... A61B 5/7257
2018/0280697 A1 10/2018 Tass et al.
2019/0099601 A1 4/2019 Torgerson
2019/0105496 A1 4/2019 Min et al.
2019/0209844 A1 7/2019 Esteller et al.
2019/0290900 A1 9/2019 Esteller et al.
2019/0366094 A1 12/2019 Esteller et al.
2019/0388692 A1 12/2019 Dinsmoor et al.
2019/0388695 A1 12/2019 Dinsmoor et al.
2020/0038660 A1 2/2020 Torgerson
2020/0101294 A1 4/2020 Torgerson
2020/0171312 A1 6/2020 Dinsmoor et al.
2020/0171313 A1 6/2020 Dinsmoor et al.
2021/0101007 A1 4/2021 Hamner et al.
2021/0121698 A1 4/2021 Dinsmoor et al.
2021/0121699 A1 4/2021 Dinsmoor et al.
2021/0121700 A1 4/2021 Dinsmoor et al.
2021/0393965 A1* 12/2021 Harhangi ............. A61N 1/0551
2022/0008730 A1 1/2022 Dinsmoor et al.
2022/0008731 A1 1/2022 Dinsmoor et al.

FOREIGN PATENT DOCUMENTS

EP 3024540 B1 10/2018
WO 2002009808 A1 2/2002
WO 2007117232 A1 10/2007
WO 2010058178 A1 5/2010
WO 2012155188 A1 11/2012
WO 2014210373 A1 12/2014
WO 2015143509 A1 10/2015
WO 2015179177 A1 11/2015
WO 2015179281 A2 11/2015
WO 2016090420 A1 6/2016
WO 2016090436 A1 6/2016
WO 2016191808 A1 12/2016
WO 2017100866 A1 6/2017
WO 2017106503 A1 6/2017
WO 2017173493 A1 10/2017
WO 2017184238 A1 10/2017
WO 2017219096 A1 12/2017
WO 2018080753 A1 5/2018
WO 2018080754 A1 5/2018
WO 2018106813 A1 6/2018
WO 2019231794 A1 12/2019

OTHER PUBLICATIONS

Abbaspour S, Fallah A. Removing ECG Artifact from the Surface EMG Signal Using Adaptive Subtraction Technique. J Biomed Phys Eng. Mar. 8, 2014;4(1):33-8. PMID: 25505766; PMCID: PMC4258854 (Year: 2014).*

Sen, Asok K., Dostrovsky, Jonathan O., Evidence of Intermittency in the Local Field Potentials Recorded from Patients with Parkinsonâ²s Disease: A Wavelet-Based Approach, Computational and Mathematical Methods in Medicine, 8, 658248, 7 pages, 2007. https://doi.org/10.1080/17486700701502363 (Year: 2007).*

"St. Jude's Prodigy Neurostimulator with Burst Technology," Medgadget, http://www.medgadget.com, Mar. 20, 2014, 4 pp.

Abejon et al., "Back pain coverage with spinal cord stimulation: A different treatment for each patient," International Neuromodulation Society, Jun. 10, 2015; 567, Abstract Only, 1 pp.

Abeloos Md "High density stimulation as an alternative to uncomfortable cervical tonic spinal cord stimulation: case report," International Neuromodulation Society 12th World Congress, Jun. 11-15, 2015, Abstract Only, 1 pp.

Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.

Breel et al., "High Density Stimulation: A novel programming paradigm for the treatment of chronic pain," International Neuromodulation Society (INS) 12th World Congress; Jun. 9, 2015, Abstract Only, 1 pp.

Crosby et al., "Modulation of activity and conduction in single dorsal column axons by kilohertz-frequency spinal cord stimulation," American Physiological Society, published online Oct. 19, 2016, 27 pp.

Cuellar et al., "Effect of High-Frequency Alternating Current on Spinal Afferent Nociceptive Transmission," Neuromodulation: Technology at the Neural Interface, vol. 16, No. 4, DOI: 10.1111/ner.12015, Nov. 6, 2012, pp. 318-327.

Cui et al., "Effect of spinal cord stimulation on tactile hypersensitivity in mononeuropathic rats is potentiated by simultaneous GABA. sub B. and adenosine receptor activation," Elsevier, Neuroscience Letters, vol. 247, Apr. 1998, pp. 183-186.

Cui et al., "Spinal cord stimulation attenuates augmented dorsal horn release of excitatory amino acids in mononeuropathy via a GABAergic mechanism," International Association for the Study of Pain, Pain, vol. 73, Oct. 1997, pp. 87-95.

De Ridder et al., "Burst spinal cord stimulation for limb and back pain," Science Direct, World Neurosurgery, vol. 80, No. 5, http://dx.doi.org/10.1016/j.wneu.2013.01.040, Nov. 2013, pp. 642-649, e641.

De Ridder et al., "Burst Spinal Cord Stimulation: Toward Paresthesia-Free Pain Suppression," Neurosurgery, vol. 66, No. 5, May 2010, pp. 986-990.

Downey, "Asynchronous Neuromuscular Electrical Stimulation," University of Florida, 2015, accessed on Jul. 18, 2016, 107 pp.

Duyvendak et al., "High density stimulation: a novel programming paradigm for the treatment of chronic back and leg pain," Abstracts, International Neuromodulation Society 12th World Congress, Neuromodulation, vol. 18, Jun. 11-15, 2015, 1 pp.

Gao et al., "Effects of spinal cord stimulation with "standard clinical" and higher frequencies on peripheral blood flow in rats," Elsevier, Brain Research, vol. 1313, doi: 10.1016/j.brainres.2009.11.072, available online Dec. 3, 2009, pp. 53-61.

Grider et al., "High Frequency (1000 Hz) Stimulation Using Commercially Available Implantable Pulse Generator," North American Neuromodulation Society, No. 198, Dec. 2013, Abstract Only, 2 pp.

Guan et al., "Spinal Cord Stimulation-induced Analgesia: Electrical Stimulation of Dorsal Column and Dorsal Roots Attenuates Dorsal Horn Neuronal Excitability in Neuropathic Rats," The American Society of Anesthesiologists, Inc., Anesthesiology, vol. 113, No. 6, Dec. 2010, pp. 1392-1405.

Guan, "Spinal Cord Stimulation: Neurophysiological and Neurochemical Mechanisms of Action" Current Pain and Headache Reports, Vo. 16, DOI 10.1007s11916-014-0260-4, Mar. 8, 2012, pp. 217-225.

Holsheimer, "Computer modelling of spinal cord stimulation and its contribution to therapeutic efficacy," International Medical Society of Paraplegia, Spinal Cord, vol. 36, Aug. 1998, pp. 531-540.

Hubscher et al., "Convergence and cross talk in urogenital neural circuitries," The American Physiological Society, Journal of Neurophysiology, vol. 110, doi: 10.1152/jn.00297.2013, Aug. 7, 2013, pp. 1997-2005.

Hunt et al. "The Molecular Dynamics of Pain Control," MacMillan Magazines, Ltd., Nature Reviews, Neuroscience, vol. 2, No. 2, Feb. 2001, pp. 83-91.

International Preliminary Report on Patentability from International Application No. PCT/US2022/070617 dated Sep. 7, 2023, 9 pp.

International Search Report and Written Opinion of International Application No. PCT/US2022/070617 dated May 19, 2022, p. 15.

Kemler et al., "Spinal Cord Stimulation in Patients with Chronic Reflex Sympathetic Dystrophy," The New England Journal of Medicine, vol. 343, No. 9, Aug. 31, 2000, pp. 618-624.

Kilgore et al., "Reversible Nerve Conduction Block Using Kilohertz Frequency Alternating Current," International Modulation Society, Neuromodulation, vol. 17, DOI: 10.1111/ner.12100, Aug. 2013, pp. 242-255.

Kumar et al., "Spinal cord stimulation versus conventional medical management for neuropathic pain: a multicentre randomised controlled trial in patients with failed back surgery syndrome," International Association for the Study of Pain, Pain, vol. 132, No. 102, Jul. 2007, pp. 179-188.

Likar et al., "High density spinal cord stimulation: a multi-center experience," Abstracts, International Neuromodulation Society 12th World Congress, Neuromodulation, vol. 18, Jun. 11-15, 2015, 1 pp.

(56) References Cited

OTHER PUBLICATIONS

Maeda et al., "Increased c-fos immunoreactivity in the spinal cord and brain following spinal cord stimulation is frequency-dependent," Elsevier, Brain Research, vol. 1259, Mar. 9, 2009, pp. 40-50.
Maeda et al., "Low frequencies, but not high frequencies of bi-polar spinal cord stimulation reduce cutaneous and muscle hyperalgesia induced by nerve injury," International Association for the Study of Pain, Pain. Vol. 138, No. 1, Feb. 2008, pp. 143-152.
Maggi et al., "Effect of urethane anesthesia on the micturition reflex in capsaicin-treated rats," Elsevier, Journal of the Autonomic Nervous System, vol. 30, No. 3, Jan. 1990, pp. 247-251.
North et al., "Clinical outcomes of 1 kHz subperception spinal cord stimulation (SCS): Results of a prospective randomized controlled crossover trial," Abstracts, International Neuromodulation Society, Neuromodulation, vol. 18, Jun. 2015, 1 pp.
North et al., "Spinal Cord Stimulation versus Repeated Lumbosacral Spine Surgery for Chronic Pain: A Randomized, Controlled Trail," Neurosurgery, vol. 56, No. 1, Jan. 2005, pp. 98-106; discussion 106-107.
Ranck Jr. et al., "Which Elements are Excited in Electrical Stimulation of Mammalian Central Nervous System: A Review," Elsevier Scientific Publishing Company, Brain Research, vol. 98, No. 3, Nov. 21, 1975, pp. 417-440.
Replogle Md. et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Sato et al., "Spinal cord stimulation reduces hypersensitivity through activation of opioid receptors in a frequency-dependent manner," European Journal of Pain, vol. 4, Apr. 2013, pp. 551-561.
Schu et al., "A Prospective, Randomised, Double-blind, Placebo-controlled Study to Examine the Effectiveness of Burst Spinal Cord Stimulation Patterns for the Treatment of Failed Back Surgery Syndrome," International Neuromodulation Society, Neuromodulation, vol. 17, No. 5, Apr. 2014, pp. 443-450.
Shechter et al., "Conventional and Kilohertz-frequency Spinal Cord Stimulation Produces Intensity- and Frequency-dependent Inhibition of Mechanical Hypersensitivity in a Rat Model of Neuropathic Pain," Anesthesiology, vol. 119, No. 2, Aug. 2013, pp. 422-432.
Sluka, et al., "High-frequency, but not low-frequency, transcutaneous electrical nerve stimulation reduces aspartate and glutamate release in the spinal cord dorsal horn," Journal of Neurochemistry, vol. 95, No. 6, Oct. 17, 2005, pp. 1794-1801.
Smith et al., "Successful Use of High-Frequency Spinal Cord Stimulation Following Traditional Treatment Failure," Stereotactic and Functional Neurosurgery, vol. 93, No. 3, Apr. 1, 2015, pp. 190-193.
Snellings et al., "Effects of stimulation site and stimulation parameters on bladder inhibition by electrical nerve stimulation," BJU International, Jul. 2012, pp. 136-143.
Song et al., "Efficacy of Kilohertz-Frequency and Conventional Spinal Cord Stimulation in Rat Models of Different Pain Conditions," International Neuromodulation Society, Neuromodulation, vol. 17, No. 3, Jan. 2014, pp. 226-234.
Stuhmeier et al., "Use of the Electrospinogram for Predicting Harmful Spinal Cord Ischemia during Repair for Throacic or Thoracoabdominal Aortic Aneurysms", Anesthesiology, vol. 79, No. 6, American Society of Anesthesiologists, Inc., Dec. 1993, pp. 1170-1176.
Sweet et al., "High Frequency vs. Burst Stimulation Patterns for Dorsal Column Stimulation: The Importance of Charge," American Association of Neurological Surgeons, Abstract, Apr. 4, 2014, 2 pp.
U.S. Appl. No. 18/038,434, filed Dec. 22, 2021, naming inventors Dinsmoor et al.
Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 2019, 10 pp.
Walter et al., "Inhibiting the Hyperrflexic Bladder With Electrical Stimulation in a Spinal Animal Mode," Neurourology and Urodynamics, vol. 12, doi: 10.1002/nau. 1930120306, Oct. 19, 1992, pp. 241-253.
Wille et al., "Altering Conventional to High Density Spinal Cord Stimulation: An Energy Dose—Response Relationship in Neuropathic Pain Therapy," International Neuromodulation Society, Neuromodulation 2016, Aug. 2016, 9 pp.
Woock et al., "Activation and inhibition of the micturition reflex by penile afferents in the cat," The American Journal of Physiology—Regulatory, Integrative and Comparative Physiology, vol. 294, Apr. 23, 2008, pp. R1880-R1889.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Youn et al., The Effect of High-Frequency Stimulation on Sensory Thresholds in Chronic Pain Patients, Stereotact Funct Neurosurg, Oct. 8, 2015, pp. 355-359.
Communication pursuant to Article 94(3) EPC from counterpart European Application No. 22710921.2 dated Jul. 2, 2025, 8 pp.

* cited by examiner

Identify Peaks

Spectrum Residual HR Seen

Derived LFP Low Frequency Energy

LOCAL FIELD POTENTIAL (LFP) SENSING FOR NEUROSTIMULATION CONTROL

RELATED APPLICATIONS

This application is a national stage entry of International Patent Application No. PCT/US2022/070617, filed Feb. 10, 2022, which claims priority to and the benefit of U.S. Provisional Patent Application No. 63/153,278, filed Feb. 24, 2021, and U.S. Provisional Application No. 63/238,290, filed Aug. 30, 2021, the entire contents of application nos. PCT/US2022/070617, 63/153,278, and 63/238,290 are incorporated by reference herein.

TECHNICAL FIELD

This disclosure generally relates to medical devices.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device. A local field potential (LFP) is a transient electrical signal generated in the nervous system and/or other tissues.

SUMMARY

In general, this disclosure describes systems, devices, and techniques for sensing and analyzing local field potentials (LFPs). In some examples, a system may be configured to sense LFPs from electrodes placed in epidural space near the spine of a patient. In some examples, the sensing electrodes may be placed near one or more dorsal root ganglia (DRG). The system may be configured to analyze the sensed LFPs and determine a change in a state of the patient, such as a physiological state (e.g., a pain state) of the patient. The system may use such analysis to update and/or recommend parameters for delivery of electrical stimulation therapy. The techniques of this disclosure may further include analyzing LFPs in a frequency domain by applying a wavelet transform or other transform to sensed LFPs. In addition, the techniques of this disclosure may include waveform processing techniques that remove or reduce electrocardiogram (ECG) and other confounding signals from the sensed LFPs to enable the system to perform more accurate analysis of the sensed LFPs.

An example system includes a memory configured to receive and store a local field potential (LFP) signal received from one or more electrodes in an epidural space of a patient, as well as processing circuitry in communication with the memory. The processing circuitry may be configured to apply a frequency transform to the LFP signal to create a frequency transformed LFP signal, and may be configured to determine a change in a physiological state of the patient from the frequency transformed LFP signal. The processing circuitry controls the one or more electrodes to sense the LFP signal from one or more electrodes placed in an epidural space of the patient, apply a frequency transform to the sensed LFP signal, and determine a change in a physiological or pain state of the patient based on the frequency transformed LFP signal. In some examples, the processing circuitry may adjust stimulation therapy delivered to the patient based on the sensed LFP signal, e.g., based on the determined change. The stimulation therapy may be, as an example, spinal cord stimulation (SCS) therapy to alleviate pain or other disorders.

In another example, this disclosure describes a method that includes receiving a local field potential (LFP) signal received from one or more electrode sin an epidural space of a patient, applying a frequency transform to the LFP signal to create a frequency transformed LFP signal, and determining a change in a physiological state of the patient from the frequency transformed LFP signal.

In another example, this disclosure describes a non-transitory computer-readable storage medium storing instructions that, when executed, causes one or more processors to receive a local field potential (LFP) signal received from one or more electrodes in an epidural space of a patient, apply a frequency transform to the LFP signal to create a frequency transformed LFP signal, and determine a change in a physiological state of the patient from the frequency transformed LFP signal.

The summary is intended to provide an overview of the subject matter described in this disclosure. It is not intended to provide an exclusive or exhaustive explanation of the systems, device, and methods described in detail within the accompanying drawings and description below. Further details of one, or more examples of this disclosure are set forth in the accompanying drawings and in the description below. Other features, objects, and advantages will be apparent from the description and drawings, and from the claims.

DETAILED DESCRIPTION

Figure 1:
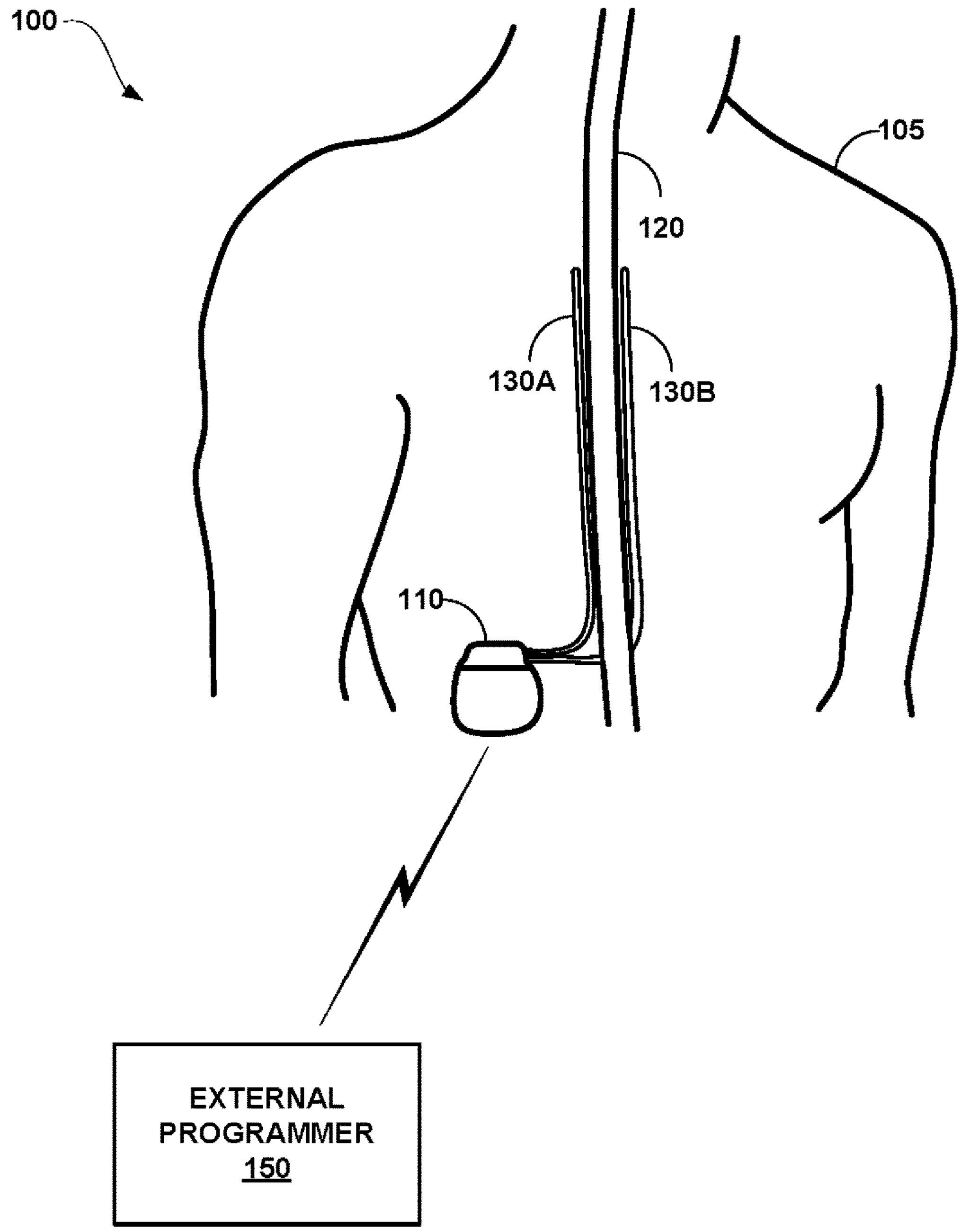
FIG. 1 is a conceptual diagram illustrating an example system that includes an implantable medical device (IMD) configured to sense a local field potential (LFP) and deliver spinal, cord stimulation (SCS) therapy and an external programmer, in accordance with one or more techniques of this disclosure.

The disclosure describes examples of medical devices, systems, and techniques to deliver electrical stimulation therapy and/or to determine a physiological state (e.g., including a pain state) of a patient based on sensed local field potentials (LFPs). Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. Electrodes implanted in a patient are positioned, e.g., via one or more implantable leads, to provide effective therapy based on the stimulation parameters.

Spinal cord stimulation (SCS) is a type of electrical stimulation therapy. SCS may include the precise delivery of electrical energy to the spinal cord, and is part of a larger class of neuromodulation. The application of SCS has been enhanced in recent years with integrated biopotential sensing and associated closed-loop control. One biopotential that has been used for closed-loop control is the evoked compound action potential (ECAP). However, other electrical signals are also present in the spinal area, such as LFPs. Spinal LFPs may be alternately described as electrospinograms.

In general, LFPs are rhythmic oscillations that may be detectable from the spine and related structures in the epidural space, such as the dorsal root ganglion (DRG), dorsal roots/rootlets, the dorsal root entry zone, and ventral roots/rootlets. Some anatomical locations may be better suited to LFP detection than others. The DRG is such an example, as recording electrodes may be located proximal to neural structures that are being assessed (e.g., immediately proximal neural structures). The characteristics of LFP's may be indicative of various disease or neurophysiologic conditions, and the LFPs may be influenced via neuromodulation, which may also be referred to as neurostimulation. LFPs are generally classified by measuring the power of the LFP in one or more spectral bands over a period of time. In some instances, LFPs may be sensed at one location to better inform, in part, neuromodulation therapy delivered at another location.

This disclosure describes systems, devices, and techniques for sensing and analyzing LFPs. In some examples, a system may be configured to sense LFPs from electrodes placed in epidural space near the spine of a patient. In some examples, the sensing electrodes may be placed near one or more DRGs. The system may be configured to analyze the sensed LFPs and determine a change in a patient state, such as a physiological state (e.g., including a pain state) of the patient. The system may use such analysis to update and/or suggest parameters for electrical stimulation therapy. The techniques of this disclosure may further include analyzing LFPs in a frequency domain, e.g., by applying a wavelet transform or other transform to sensed LFPs. In addition, in some examples, the techniques of this disclosure may include waveform processing techniques that remove electrocardiogram (ECG) and other confounding signals from the sensed LFPs so that more accurate analysis of the sensed LFPs may be performed. For example, removal of confounding signals may enable the system to identify one or more characteristics of LFPs that can be used to determine a particular physiological state.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal that may have a sinusoidal waveform or other continuous waveform.

FIG. 1 is a conceptual diagram illustrating an example system 100 that includes an implantable medical device (IMD) 110 configured to sense LFPs and deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in the example of FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. In the context of this disclosure, leads 130 and the accompanying electrodes may be considered part of sensing circuitry considered to sense LFPs.

IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 6) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as circuitry and a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. In examples of this disclosure, leads 130 may be placed in the epidural space of the spine of patient 105, such as near one or more of a dorsal root ganglion (DRG), dorsal roots/rootlets, dorsal root entry zone, and/or ventral roots/rootlets in order to sense LFPs. In general, leads 130 may be positioned in a lateral placement from the midline.

One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. In addition, as will be explained in more detail below, leads 130 may further be configured to sense LFPs in an epidural space of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied to select any subset of electrodes for stimulation and/or sensing. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having eight ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy delivered by IMD 110 through the electrodes of leads 130 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input. As will be explained in more detail below, in other examples, IMD 110 may be configured to determine stimulation parameters based on LFPs sensed in the epidural space of patient 105.

In some examples, IMD 110 may deliver stimulation pulses that contribute to therapy perceived by patient 105. IMD 110 may detect ECAP signals elicited by these stimulation pulses. In other examples, stimulation pulses configured to provide therapy may prevent IMD 110 from detecting ECAP signals (e.g., because the pulse width of the stimulation pulses are long enough to interfere with propagating ECAP signals). Therefore, if control pulses (e.g., pulses that may or may not contribute to therapy) separate from informed pulses configured to provide therapy are needed to elicit a detectable ECAP signal, system 100 may employ an ECAP test stimulation program that defines stimulation parameter values that define control pulses delivered by IMD 110 through at least some of the electrodes of leads 130.

These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses. The stimulation defined by each ECAP test stimulation program may not be intended to provide or contribute to therapy for the patient, but the patient may perceive the control pulses in some examples. In addition, the ECAP test stimulation program may define the control pulses used for each sweep of pulses that are used to detect a change in an ECAP signal that is indicative of the associated lead having migrated from its original position.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced adjacent to spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which causes a tingling sensation that may reduce the perception of pain by patient 105, and thus, provide efficacious therapy results.

IMD 110 is configured to generate and deliver electrical stimulation therapy to a target stimulation site within patient 105 via the electrodes of leads 130 to patient 105 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

Furthermore, IMD 110 may be configured to deliver control stimulation to patient 105 via a combination of electrodes of leads 130, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes. Since control stimulation pulses can be delivered in an interleaved manner with informed pulses (e.g., when the pulses configured to contribute to therapy interfere with the detection of ECAP signals or pulse sweeps intended to detect migration of leads 130 via ECAP signals do not correspond to pulses intended for therapy purposes), a clinician and/or user may select any desired electrode combination for informed pulses.

Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 can deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as electrical stimulation therapy (e.g., informed pulses) and/or control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

In addition to, or instead of, the ECAPs-related techniques described above for sensing the effects of electrical stimulation therapy and updating parameters, this disclosure further describes techniques for sensing and analyzing LFPs for determining the efficacy of electrical stimulation therapy, for updating parameters for electrical stimulation therapy, and/or for detecting changes in a physiological state (e.g., including a pain state) of a patient. As described above, one biopotential that has been used for closed-loop control is the ECAP. However, other electrical signals are also present in the spine and associated nerve structures, such as LFPs.

Spinal LFPs may be alternately described as electrospinograms. In general, LFPs are rhythmic oscillations that may be detectable from the spine and related structures in the epidural space, such as the dorsal root ganglion (DRG), dorsal roots/rootlets, the dorsal root entry zone, and ventral roots/rootlets. Some anatomical locations may be better suited to LFP detection than others. The DRG is such an example, as recording electrodes may be located proximate neural structures being assessed (e.g., immediately proximate neural structures). LFPs may be considered a type of neural noise measurements, which may be indicative of spontaneous activity. Pain is associated with an increase in spontaneous activity of pain-carrying primary fibers in the periphery, as well as cells in the dorsal root ganglion (DRG). When recorded with electrodes of leads 130 (e.g., macro-electrodes), the spontaneous activity can show up as an increase in noise levels, as well as possibly a peak in particular frequency. The characteristics of LFP's may be indicative of various disease or neurophysiologic conditions, and the LFPs may be influenced via neuromodulation. LFPs are generally classified by measuring the power of the LFP in one or more spectral bands. In some instances, LFPs may be sensed at one location to better inform, in part, neuromodulation therapy delivered at another location.

In some examples, IMD 110 may be configured to sense LFPs from electrodes on leads 130 placed in epidural space near the spine of patient 105. In some examples, the sensing electrodes may be placed near one or more DRGs, dorsal roots/rootlets, dorsal root entry zones, and/or ventral roots/rootlets. In some examples, the electrodes on leads 130 may be macro-electrodes. In addition or alternatively, the electrodes on leads 130 may be arranged in a wide bi-pole configuration. In some examples, leads 130 may be placed in the epidural space of patient 105 laterally along the mid-line of the spine. In addition or alternatively, leads 130 may be arranged head to tail.

In general, IMD 110, external programmer 150, or another computing device may be configured analyze the sensed LFPs and determine a change in a physiological state (e.g., including a pain state) of patient 105. IMD 110 and/or external programmer 150 may be configured to use such analysis to update and/or suggest parameters for electrical stimulation therapy. For example, IMD 110 and/or external programmer 150 may change pulse width and/or amplitude of neuromodulation.

The techniques of this disclosure may further include analyzing LFPs in a frequency domain by applying a wavelet transform or another transform to sensed LFP signals. In addition, the techniques of this disclosure may include waveform processing techniques that remove electrocardiogram (ECG) and other confounding signals from the sensed LFPs so that more accurate analysis of the sensed LFPs may be performed.

As described above, ECAP analysis is a temporal analysis based on response from a stimulus. An ECAP measurement is a time-bounded event. However, an LFP is generally always present, though the amplitude of LFPs can be influenced by stimulation. ECAP and LFP detection and analysis are generally different. As such, LFP sensing may include placing leads in atypical target areas. That is, the electrodes of leads 130, and even leads 130 themselves, do not need to be placed proximally to a particular area where pain is thought to arise. In addition, IMD 110 and/or external programmer 150 may not need to analyze LFPs in any specific time window to determine a change in a physiological state (e.g., including a pain state). LFPs are present with or without stimulation. IMD 110 may be configured to measure voltage differences between two electrodes to sense LFPs. In general, intrinsic LFPs (e.g., LFPs present without stimulation) have a relatively low amplitude.

IMD 110 and/or external programmer 150 may use sensed LFPs to assess the types of neural fibers activated, the extent of neural activation, and the degree of hyper- or hypo-polarization. In general, IMD 110 and/or external programmer 150 may use the detection of LFPs as markers for conditions or physiological states that cause pain. IMD 110 and/or external programmer 150 may then use the detected changes in physiological states (e.g., including a pain states) to determine and/or suggest treatments, update treatment parameters (e.g., update parameters for electrical stimulation therapy), and/or output sensed LFPs for further study.

Physical problems with the spinal cord or nervous system that cause spurious pain signals may be detectable in LFPs. Further, LFPs may be indicative of a wide range of physiologic or biochemical processes. LFPs may be indicative of slower (holistic) changes in neurological processes. Some of these may include: degree and extent of pain (neuralgia), degree of over/under sensitivity to pain (hyper- or hypoalgesia), susceptibility of a neural target to transmit or receive information, either electrically or biochemically, susceptibility of a neural target to respond therapeutically to electrical stimulation, either proximal to the location being sensed or at a distant location, or biochemical state (e.g., the up/down regulation of pain-relevant genomes, availability and susceptibility to release of signaling chemicals such as acetylcholine, Substance P, glutamate, dopamine, GABA, histamine, norepinephrine, serotonin, and glycine).

In one or more techniques of this disclosure, IMD 110 and/or external programmer 150 may be configured to analyze a sensed LFP waveform to determine LFP characteristics that are indicative of appropriate neuromodulation to the neural target (e.g., nerves in or near the spine). The LFP characteristics may also indicate if the neuromodulation is not appropriate; for instance, the neuromodulation is no longer delivered to the correct anatomical location because of lead migration. IMD 110 and/or external programmer 150 may determine the LFP characteristics empirically or by a machine learning process whereby neuromodulation parameters are varied until the desired response (such as hyperalgesia suppression) is obtained. IMD 110 and/or external programmer 150 may then capture the LFP for use as a template from that point forward. Once the LFP template is obtained, IMD 110 and/or external programmer 150 may be configured to vary electrical stimulation parameters to maintain the desired response.

Example characteristics of an LFP waveform include a voltage amplitude in one or more spectral bands and/or power in one or more spectral bands. Other example characteristics may include comparisons, such as ratios of power and/or voltage between two different spectral bands. In other examples, IMD 110 and/or external programmer 150 may be configured to measure single spike potentials in an LFP waveform (e.g., LFP signal). Spontaneous activity may occur during pain events. IMD 110 and/or external programmer 150 may be configured to measure LFPs from a DRG near the spinal cord over time to detect pain events. For example, IMD 110 and/or external programmer 150 may be configured to measure over a period of time (e.g., measure percent increase to detect a state change). Measuring over time does not relate to spike recording, but rather a wider measurement. The period of time may be over the course of hours, including up to 24 hours or more.

In addition to analyzing LFPs to detect changes in patient state and/or to update electrical stimulation therapy parameters, IMD 110 and/or external programmer 150 may be configured to use other sensed or input information to make therapy decisions. For example, characteristics of LFPs in addition to one or more of ECAP data, cardiac data (e.g., heart rate), respiratory data (e.g., respiration rate), and accelerometry data may be used to determine changes in patient state and/or to update electrical stimulation therapy parameters, e.g., based on the determined patient state or patient state change. For example, heart rate and respiratory rate could both feed into a multiparameter composite marker for pain. Cardiac signals can also be used to derive heart rate variability (HRV) that has been shown to have some association with pain (low HRV being a marker of elevated sympathetic tone and hence worse pain status).

IMD 110 may be configured to perform recordings of LFP signals in a position that facilitates the measurement (e.g., patient 105 is supine). Patient 105 can be automatically initiated into measurement and asked to lie down. In another example, the position can be detected from an accelerometer. Relatively long measurements may be taken and averaged, in some examples. In addition, measurements may be taken when the spinal cord is not moving. This patient non-moving status can be determined by the ECAPs remaining relatively constant.

The LFP measurements may be corrupted by ECG signals and other confounding signals detected from the patient along with the LFP signals. Consequently, IMD 110 and/or external programmer 150 may be configured to remove ECG signals and other confounding signals from the sensed LFP waveforms. For example, IMD 110 and/or external programmer 150 may identify ECG peaks and subtract them from the LFP waveform.

In some examples, recordings of LFPs would optimally be performed in wider bipole configurations. If stimulation is occurring, IMD 110 may be switched to active discharge during measurement to reduce stimulation artifact. Similarly, if the stimulation is duty-cycled, IMD 110 may be configured to avoid duty-cycling during the measurements (e.g., ideally make measurements in the off phase). Because the source of potentials of interest, in some examples, is likely to be near the DRG, this recording may be conducted in the laterally placed leads, as well as in the DRG placed electrodes.

In summary, IMD 110 and/or external programmer 150 may be configured to use several different signal processing methods, including:

a. Removal of an ECG waveform from LFPs;
b. Removal of the ECAP signal;
c. Removal of the simulation signal; or
d. Compensation for movement of electrodes (e.g., accelerometer, ECAPs, etc.).

In general, IMD 110 may be configured to receive and store a local field potential (LFP) signal received from one or more electrodes in an epidural space of a patient. IMD 110 and/or other processing circuitry (e.g., external programmer 150) may be configured to apply a frequency transform to the LFP signal to create a frequency transformed LFP signal, and determine a change in a physiological state (e.g., including a pain state) of the patient from the frequency transformed LFP signal. IMD 110 may further be configured to perform the confounding signal removal techniques described below.

Figure 2:
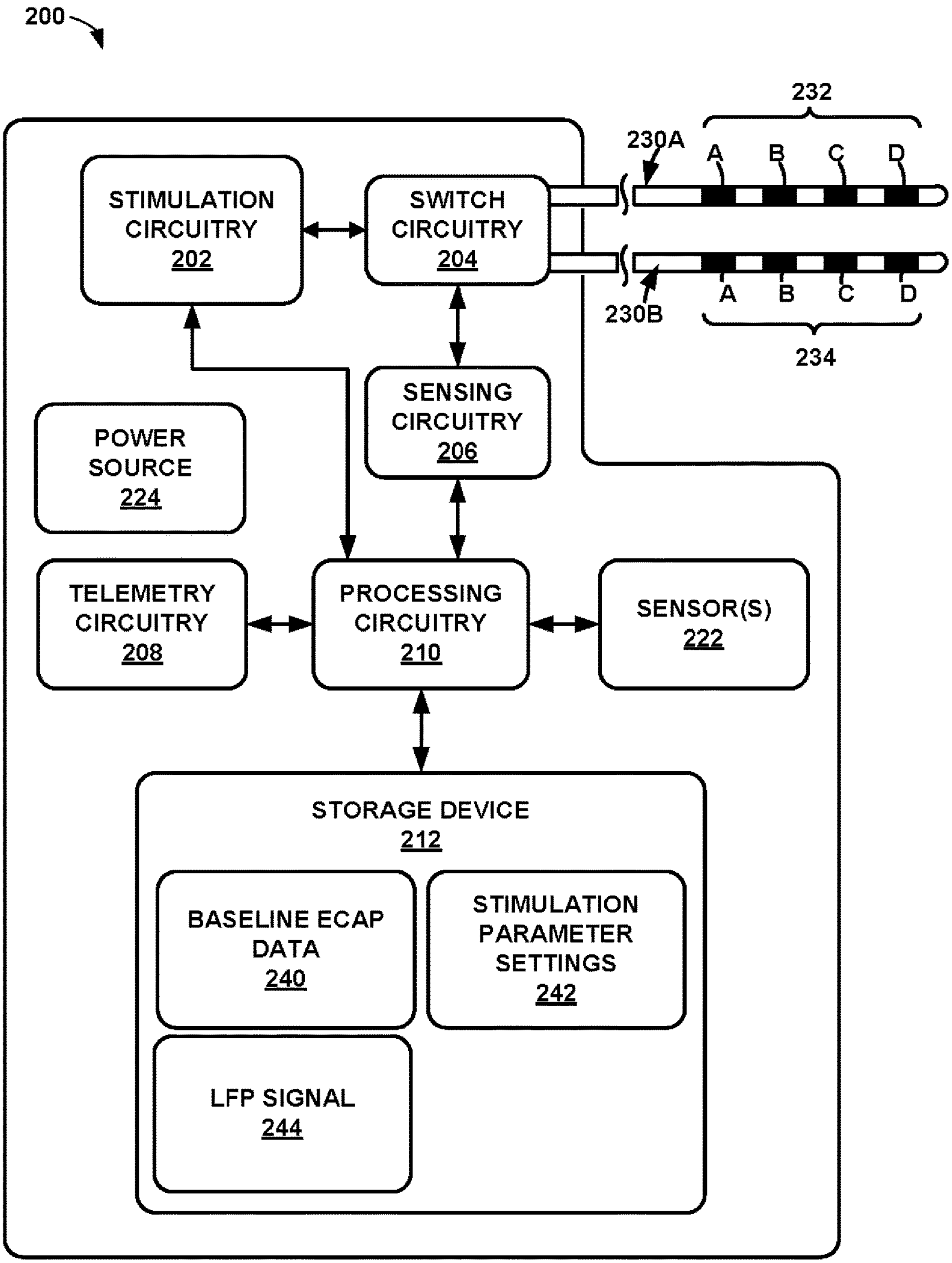
FIG. 2 is a block diagram illustrating an example configuration of components of an IMD, in accordance with one or more techniques of this disclosure.

FIG. 2 is a block diagram illustrating an example configuration of components of an IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, telemetry circuitry 208, processing circuitry 210, storage device 212, sensor(s) 222, and power source 224. Leads 230A and 230B (collectively, leads 230) may be an example of leads 130 of FIG. 1. Leads 230 may include one or more electrodes 232 and electrodes 234. In the context of this disclosure, the term "sensing circuitry" may refer to leads 230, sensing circuitry 206, and/or the combination of sensing circuitry 206 and leads 230.

In the example shown in FIG. 2, storage device 212 stores baseline ECAP data 240, LFP signal 244, and stimulation parameter settings 242 in separate memories within storage device 212 or separate areas within storage device 212. LFP signal 244 may include the sensed LFP as well as the LFP after frequency domain transform and confounding signal (e.g., ECG) extraction. In some examples, stimulation parameter settings 242 may include stimulation parameter values (sometimes referred to as "sets of therapy parameters") for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulation electrode combination, electrode polarity, current or voltage amplitude, pulse width, pulse rate, and pulse shape.

In some examples, stimulation parameter settings 242 may store a primary set of therapy parameters for when leads 230 are in an implant location and a secondary set of therapy parameters for when one of leads 230 has migrated. Storage device 212 may also store ECAP test stimulation programs, as part of stimulation parameter settings 242 or as a separate memory area, that defines values for a set of electrical stimulation parameters (e.g., a control stimulation parameter set) configured to elicit a detectable ECAP signal, such as a stimulation electrode combination, electrode polarity, current or voltage amplitude, pulse width, pulse rate, and pulse shape. ECAP test stimulation programs may also have additional information such as instructions regarding when to deliver control pulses based on the pulse width and/or frequency of the informed pulses defined in stimulation parameter settings 242.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or direct sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 is configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP signals and/or LFP signals. In some examples, sensing circuitry 206 detects ECAPs and/or LFPs from a particular combination of electrodes 232, 234. In some cases, the particular combination of electrodes for sensing ECAPs and/or LFPs includes different electrodes than a set of electrodes 232, 234 used to deliver stimulation pulses. Alternatively, in other cases, the particular combination of electrodes used for sensing ECAPs and/or LFPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 6) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234. One or more switches may still be present to connect or disconnect sensing circuitry 206 from respective current sources if needed to, for example, reduce the likelihood of circuit damage from the delivery of current to electrodes.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. In some examples, one or more of electrodes 232 and 234 are suitable for sensing the ECAPs and/or LFPs. For instance, electrodes 232 and 234 may sense the voltage amplitude of a portion of the ECAP and/or LFP signals, where the sensed voltage amplitude, such as the voltage difference between features within the signal, is a characteristic of the ECAP and/or LFP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store LFP signal 244, baseline ECAP data 240, LFP signal 244, and stimulation parameter settings 242.

As described, electrodes 232 and 234 may be the electrodes that sense the characteristic value of the ECAP and/or LFP signal. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity or posture, and processing circuitry 210 may increase the frequency of control pulses, ECAP sensing, and/or LFP sensing in response to detecting increased patient activity or posture.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

In general, IMD 200 is an example of a device that may be configured to receive and store a local field potential (LFP) signal received from one or more electrodes in an epidural space of a patient. IMD 200 may be configured to apply a frequency transform to the LFP signal to create a frequency transformed LFP signal, and determine a change in a physiological state (e.g., including a pain state) of the patient from the frequency transformed LFP signal. IMD 200 may further be configured to perform the confounding signal removal techniques described below.

Figure 3:
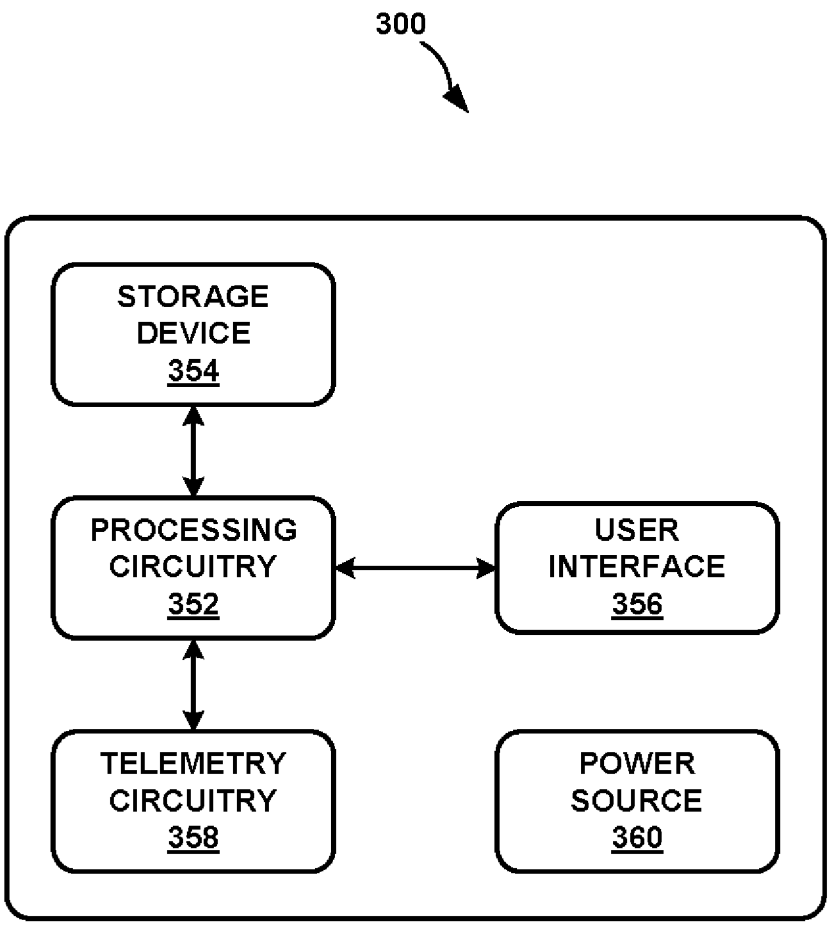
FIG. 3 is a block diagram illustrating an example, configuration of components of an example external programmer, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode pattern, or receive a user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110 of FIG. 1). For example, storage device 354 may store ECAP and/or LFP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, such as a representation of the LFP signal, a representation of the frequency domain transformed LFP signal, a representation of the frequency domain transformed, LFP signal where confounding signals have been removed, a representation of the baseline ECAP signal, a representation of the most recent captured ECAP signal, a measure of the latency between stimulation and ECAP detection, and/or an alert indicative of the migration state of leads 130. User interface 356 may also receive user input (e.g., indication of when the patient perceives a stimulation pulse) via user interface 356. The input may be, for example, in the form of pressing a button on a keypad or selecting an icon from a touch screen. The input may request starting or stopping electrical stimulation, the input may request a new spatial electrode pattern or a change to an existing spatial electrode pattern, or the input may request some other change to the delivery of electrical stimulation. During a calibration process of obtaining ECAP and/or LPF signals for different posture states, user interface 356 may present the posture state that the patient should assume, and user interface 356 may receive user input confirming that the patient is in the requested posture state. The calibration process may also incorporate radiographic data such as x-rays, fluorography, CT scans, MR images or the like, and relate those data to the ECAP and/or LFP signal. In other examples, user interface 356 may receive user input indicating the posture state that the patient is in and generate the relationship of the detected ECAP and/or LFP characteristic values obtained during the calibration (e.g., the calibrated growth curve) for that indicated posture state.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

In general, external programmer 300 is an example of a device that may be configured to receive and store a local field potential (LFP) signal received from one or more electrodes in an epidural space of a patient. External programmer 300 may be configured to apply a frequency transform to the LFP signal to create a frequency transformed LFP signal, and determine a change in a physiological state (e.g., including a pain state) of the patient from the frequency transformed LFP signal. External programmer 300 may further be configured to perform the confounding signal removal techniques described below.

Figure 4:
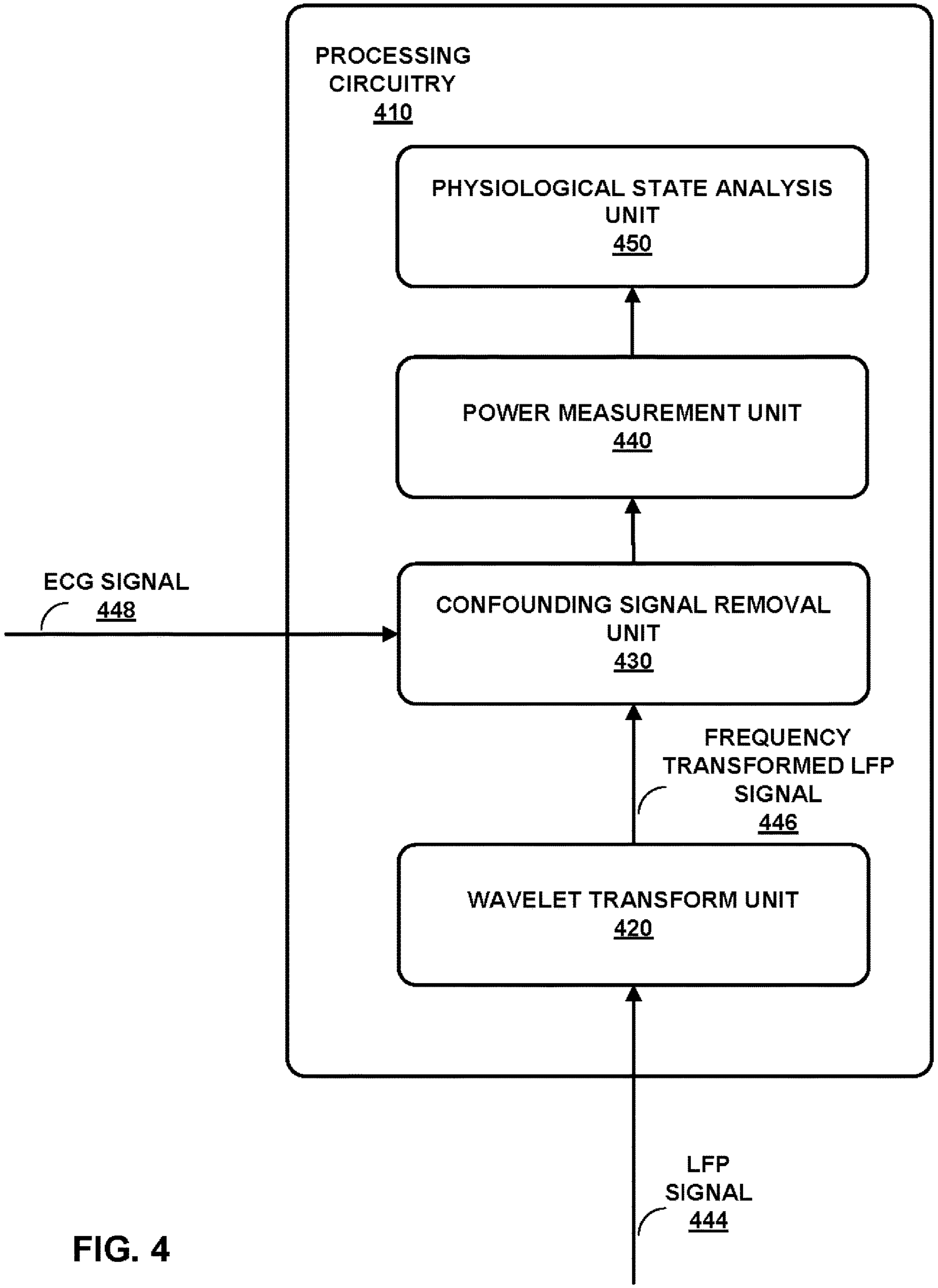
FIG. 4 is a block diagram illustrating an example of the processing circuitry of FIG. 2 in more detail.

FIG. 4 is a block diagram illustrating an example of the processing circuitry of FIG. 2 in more detail. Processing circuitry 410 may be one example implementation of processing circuitry 210 of FIG. 2. In other examples, processing circuitry 410 may be an example of processing circuitry 352 of external programmer 350 of FIG. 3. In the example of FIG. 4, processing circuitry 410 includes wavelet transform unit 420, confounding signal removal unit 430, power measurement unit 440, and physiological state analysis unit 450.

In general, processing circuitry 410 includes any suitable arrangement of hardware, alone or in combination with software and/or firmware, to perform the techniques attributed to processing circuitry 410. In various examples, processing circuitry 410 may include one or more processors, such as one or more microprocessors, DSPs, ASICs, FPGAs, or any other equivalent integrated or discrete logic circuitry, as well as any combinations of such components. Processing circuitry 410 also, in various examples, may include a storage device, such as RAM, ROM, PROM, EPROM, EEPROM, flash memory, a hard disk, a CD-ROM, including executable instructions for causing the one or more processors to perform the actions attributed to them. Moreover, although the structural units of processing circuitry 410 are described as separate units, in some examples the structural units of processing circuitry 410 are functionally integrated. In some examples, the structural units of processing circuitry 410 correspond to individual hardware units, such as ASICs, DSPs, FPGAs, or other hardware units.

In one example of the disclosure, processing circuitry 410 may receive LFP signal 444. LFP signal 444 may be received from one or more electrodes connected to sensing circuitry (e.g., leads 130 of FIG. 1), where the one or more electrodes are placed in an epidural space of a patient (e.g., patient 105 of FIG. 1). In some examples, processing circuitry 410 may be configured to initiate a measurement of LFP signal 444 when the patient is in a supine position. In one example, processing circuitry 410 may be configured to initiate the measurement of LFP signal 444 in response to an accelerometer detection of the supine position.

In other examples, processing circuitry 410 may be configured to initiate the measurement of LFP signal 444 in response to a detection of a constant ECAPs signal. A constant ECAPs signal may be an ECAPs signal that fluctuates less than a threshold amount. In general, a high ECAPs measurement may make analysis of LFP signal 444 difficult. Accordingly, in another example, processing circuitry 410 may be configured to switch an electrical stimulation therapy to active discharge when initiating the measurement of LFP signal 444. Processing circuitry 410 may also be configured to initiate the measurement of LFP signal 444 in response to an off phase of a duty cycle of an electrical stimulation therapy.

As described above, the sensing circuitry used to sense LFP signal 444 may be connected to leads having one or more macro-electrodes. The leads may be arranged in a wide bi-pole configuration and/or may include laterally placed leads from mid-line of a spine of the patient. The sensing circuitry may optionally be connected to two leads arranged head to tail. In one example, the leads placed on a DRG.

Wavelet transform unit 420 may be configured to perform a frequency transform on LFP signal 444 to generate frequency transformed LFP signal 446. In one example, wavelet transform unit 420 may be configured to perform a wavelet transform on LFP signal 444. Wavelet transforms have been shown to represent the spectral power of LFP signals more accurately. However, wavelet transform unit 420 may be configured to apply different frequency transformation techniques to LFP signal 444 in other examples.

Confounding signal removal unit 430 may be configured to remove one or more confounding signals from frequency transformed LFP signal 446. In this context, a confounding signal may be any signal that may obscure frequency transformed LFP signal 446 and/or make analysis of frequency transformed LFP signal 446. In some applications, the sensing circuitry may sense one or more confounding electrical signals generated by the body and/or generated by electrical devices with the body. Example confounding signals may include ECAPs signals, a stimulation signal, and/or ECGs. As discussed above, in some examples processing circuitry 410 may be configured to initiate the measurement of LFP signal 444 in a manner that reduces the impact of ECAPs signals. However, ECG signals may still be present.

As such, confounding signal removal unit 430 may be configured to remove ECG signal 448 from frequency transformed LPF signal 446. In one example, to remove ECG signal 448 from frequency transformed LFP signal 446, confounding signal removal unit 430 may be configured to identify peaks in ECG signal 448, and subtract the ECG peaks from frequency transformed LFP signal 446. In this example, confounding signal removal unit 430 may be configured to frequency transform ECG signal 448 and identify peaks in certain spectral bands. Confounding signal removal unit 430 may then remove the peaks of ECG signal 448 in the identified spectral bands from the corresponding spectral bands of frequency transformed LFP signal 446. Wavelet transforms may be used as a feature detector to identify the QRS complex intrinsic to ECG signals. Once the location of the QRS complex is identified, confounding signal removal unit 430 may be configured to ignore in-band spectral content (such as 5 Hz-23 Hz) for the approximately 70-110 ms that corresponds to the width of the QRS complex. Confounding signal removal unit 430 may then assess LFP's that are out of band to the QRS complex, such as those at approximately 100 Hz, at any point. In other cases, confounding signal removal unit 430 may be configured to identify features other than the QRS complex, such as the p- or t-waves, and temporally isolate such features using a similar approach. In some examples, removal of confounding signals may be optional.

In addition, confounding signal removal unit 430 may be configured to remove an ECG in the time domain. Confounding signal removal unit 430 may be configured to identify a QRS complex in the ECG using template matching. Upon identification, confounding signal removal unit 430 may be configured to identify a patient specific QRS complex based on synchronous averaging. Confounding signal removal unit 430 may then subtract the patient specific QRS template from the incoming signal prior to frequency analysis. The QRS complex is known to vary with time, e.g. with breathing. Thus, subtraction of the QRS complex may not be perfect. Additionally, therefore, the frames including QRS complex can be excluded from analysis. In contrast, T waves and P waves frequently show less variability relative to the QRS complex. Confounding signal removal unit 430 may be configured to subtract the T wave and P wave components of the waveform from the time waveform and utilized. More generally, measures of quality of fit of the template, such as sample by sample variance from beat to beat, can be used to determine whether frames of information are included or excluded from the analysis.

Next, power measurement unit 440 may be configured to measure the power of frequency transformed LFP signal 446 in one or more spectral bands, without or without confounding signal removal. In one example, power measurement unit 440 is configured to measure the power of frequency transform LFP signal 446 in one or more spectral bands below 200 Hz. Lower frequency power in frequency transform LFP signal 446 may be more indicative of a change in a physiological state (e.g., including a pain state) in some examples. In other examples, power measurement unit 440 is configured to measure the power of frequency transform LFP signal 446 in one or more spectral bands below 80 Hz. Power measurement unit 440 may be configured to measure the power of frequency transform LFP signal 446 of different time periods. In one example, power measurement unit 440 is configured to measure the power of frequency transform LFP signal in one or more spectral bands over a period of time. As described above, it may be beneficial to measure power over a relatively long period of time (e.g., over several hours) as changes in measured power may be more indicative of a change in a physiological state (e.g., including a pain state) of the patient.

After the power of frequency transformed LFP signal 446 has been measured, physiological state analysis unit 450 may be configured to determine a change in a physiological state (e.g., including a pain state) of the patient based on the measured power of frequency transformed LFP signal 446. The physiological state of the patient may include one or more of a degree or extent of pain, a degree of sensitivity to pain, a susceptibility of a neural target to transmit or receive information, a susceptibility of a neural target to respond therapeutically to electrical stimulation, or a biochemical state. To determine the change in the physiological state (e.g., including a pain state) of the patient, physiological state analysis unit 450 may be configured to compare respective powers of frequency transformed LFP signal 446 in two or more spectral bands, and determine the change in the physiological state of the patient based on the comparison. In other examples, physiological state analysis unit 450 may be configured to determine the change in the physiological state of the patient based on a measured power in a single spectral band at a single instance of time. In other examples, physiological state analysis unit 450 may be configured to determine the change in the physiological state of the patient based on an average and/or mean of the measured power one or more spectral bands over a period of time. In still other examples, physiological state analysis unit 450 may be configured to determine the change in the physiological state of the patient based on a change of measured power in one or more spectral bands over a period of time.

In some examples of the disclosure, these changes in the physiological state of the patient may be assessed relative to a library of LFP's from normal physiology patients. For example, power in a spectral band that is within about 1%, about 2%, about 5%, about 10%, about 20%, about 30%, about 40%, or more than 50% of that classified in the patients without chronic pain. In other examples, the baseline "no-pain" state may be assessed when reported as such by the patient or after administration of analgesic agent, such as DRG stimulation, spinal cord stimulation, application of a nerve blocker (e.g., lidocaine), or a systemic opioid (e.g., fentanyl).

In some examples, physiological state analysis unit 450 may be configured to determine the change in the physiological state of the patient based on one or more signals in addition to frequency transformed LFP signal 446. For example, physiological state analysis unit 450 may use both LFP and ECAPs data to determine a change in the physiological state of the patient. In some examples, the LFP signal may be used as a confidence factor for pain states determined through ECAPs techniques, or vice versa. In other examples, physiological state analysis unit 450 may use both frequency transformed LFP signal 446 and ECG signal 448 data to determine a change in the physiological state of the patient. For example, a change in heart rate and/or a change in the ECG waveform, in conjunction with measured power in frequency transformed LFP signal 446, may be indicative of a change in the physiological state of the patient. Other example signals that may be in conjunction with an LFP signal may include an output of an accelerometer and/or a respiration measure.

In some examples, physiological state analysis unit 450 may be further configured to determine one or more parameters for electrical stimulation therapy based on the determined change in the physiological state (e.g., including a pain state) of the patient. Parameters of electrical stimulation therapy may include a frequency, an amplitude, a pulse width, and/or a pulse shape of electric pulses. In some examples, the electrical stimulation is therapeutically effective if it results in suppression of a given LFP of about 50%. The amplitude of a given electrical stimulation therapy program may be ramped up to a clinically dictated maximum level. If no suppression is seen in the LFP, a new stimulation program may be selected and the amplitude sweep may be repeated. In other examples, other parameters may be swept, such as stimulation pulse width or frequency.

Figure 5:
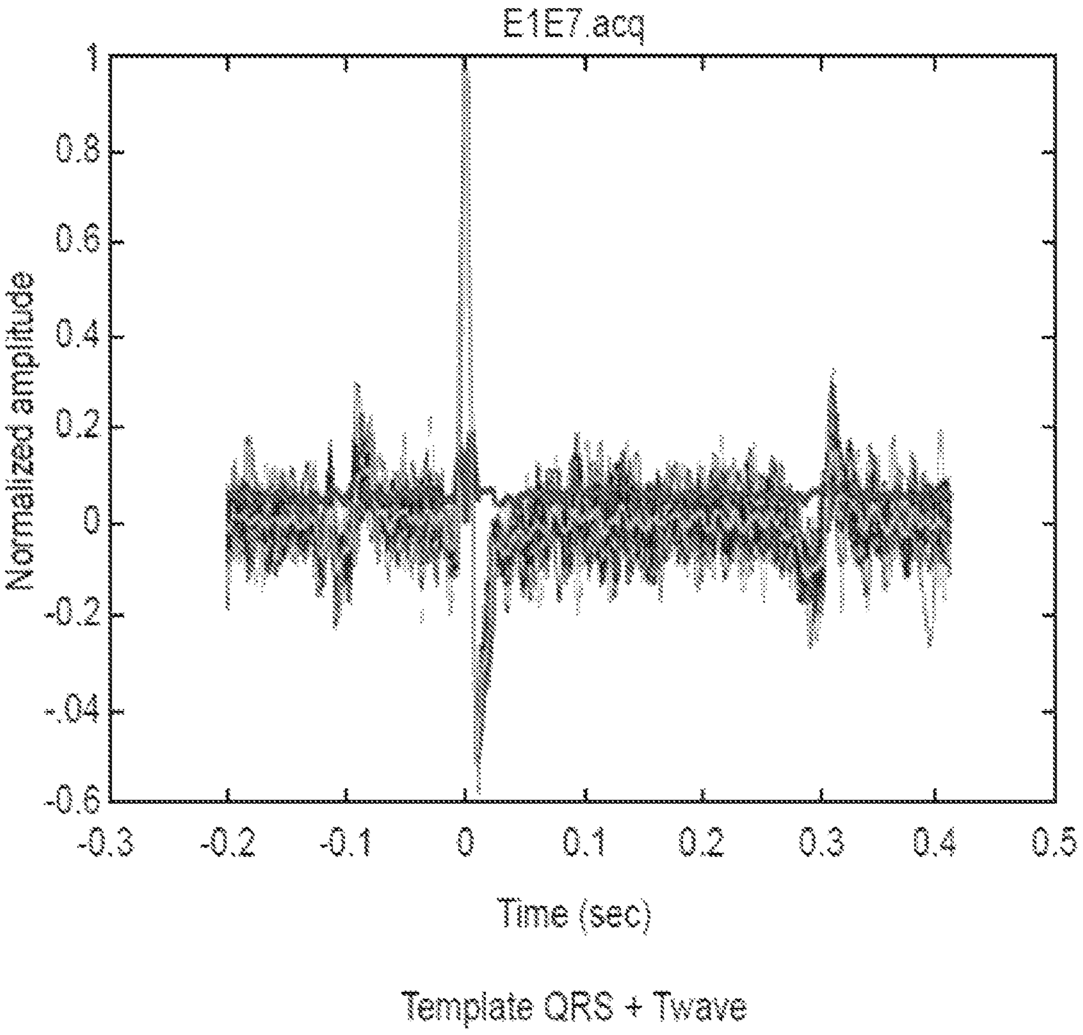
FIG. 5 illustrates an example waveform captured by electrodes coupled to an IMD.
Figure 6:
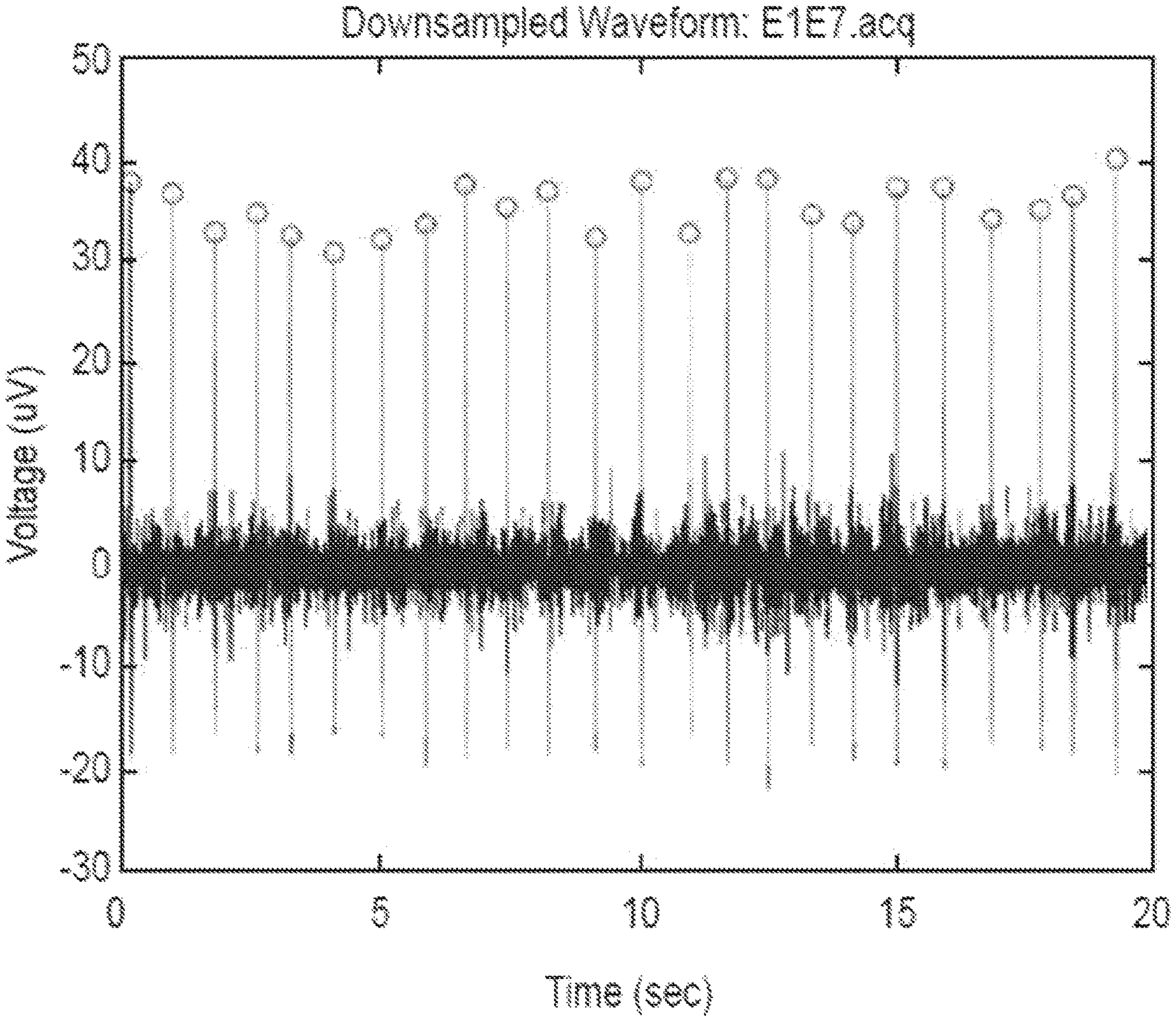
FIG. 6 illustrates example peaks identified in a down-sampled version of the waveform of FIG. 5.
Figure 7:
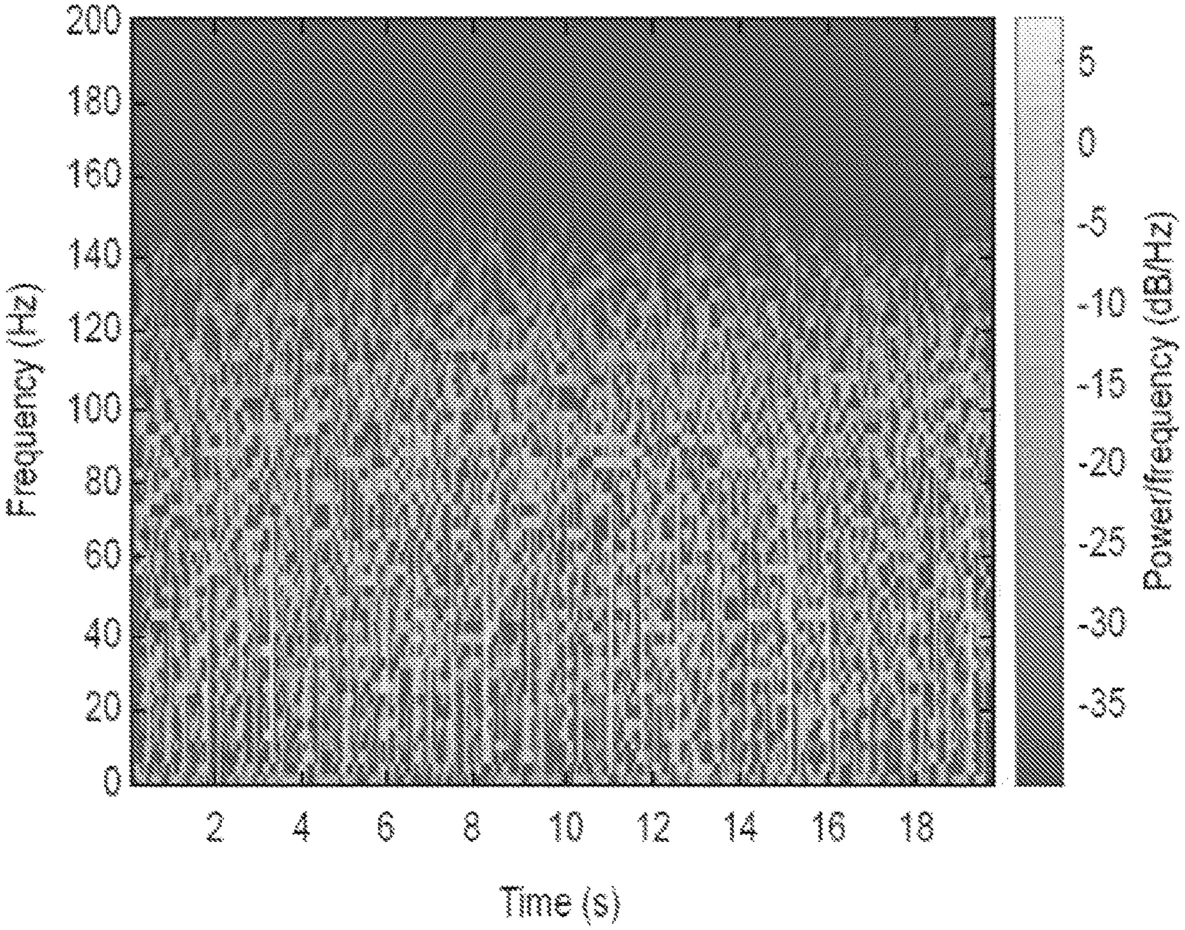
FIG. 7 illustrates the waveform of FIG. 6 in the frequency domain.

FIGS. 5-7 illustrate example LFP waveforms with a confounding ECG signal. As described above, the waveform that includes the LFP signal may also include an ECG waveform comprising a QRS complex and a T wave. FIG. 5 illustrates an example waveform captured by electrodes of an IMD. IMD 110 and/or external programmer 150 may be configured to identify residuals and subtract based on peaks. For example, IMD 110 and/or external programmer 150 may perform a transform on the LFP waveform and identify peaks in particular frequencies and/or frequency bands. FIG. 6 illustrates example peaks identified in a downsampled version of the waveform of FIG. 5.

FIG. 7 illustrates the waveform of FIG. 6 in the frequency domain. In one example, IMD 110 and/or external programmer 150 may use a wavelet transform to transform the LFP waveform to the frequency domain, though other types of transforms may also be used. In general, wavelet transforms may be better for detecting lower frequency changes relative to a fast Fourier transform (FFT). As described above, in some examples, IMD 110 and/or external programmer 150 may be configured to analyze the frequency transformed (e.g., by wavelet transform) LFP signal (e.g., after confounding signal extraction) at certain spectral bands. For example, analysis may occur below 200 Hz, or 80 Hz and below. In other examples, both relatively low and relatively high frequency bands may be analyzed. IMD 110 and/or external programmer 150 may be configured to determine electrical stimulation parameters for particular electrodes where peak amplitudes are detected in the frequency domain transformed LFP signals, where stimulation may suppress the peak.

Figure 8:
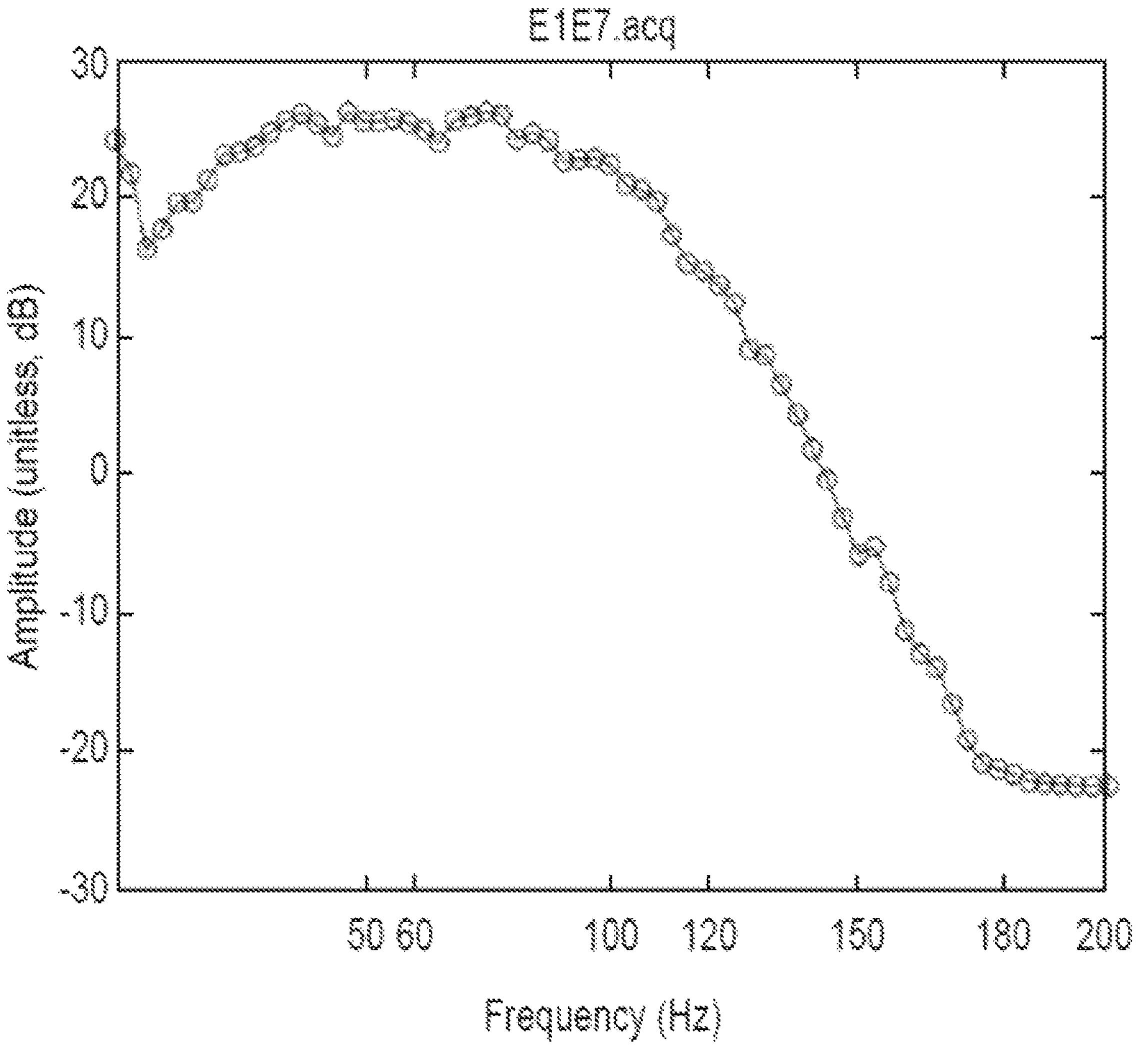
FIG. 8 illustrates the waveform of FIG. 7 with confounding signals removed to show an example local field potential (LFP).

FIG. 8 illustrates the waveform of FIG. 7 with confounding signals removed to show an example local field potential (LFP). ECAPS may also be a confounding signal and could be removed. Wavelet transforms may be useful for removing ECAPs. In general, IMD 110 and/or external programmer 150 may be configured remove waveforms where subtraction does not work well for the analysis (e.g., around a QRS complex).

Figure 9:
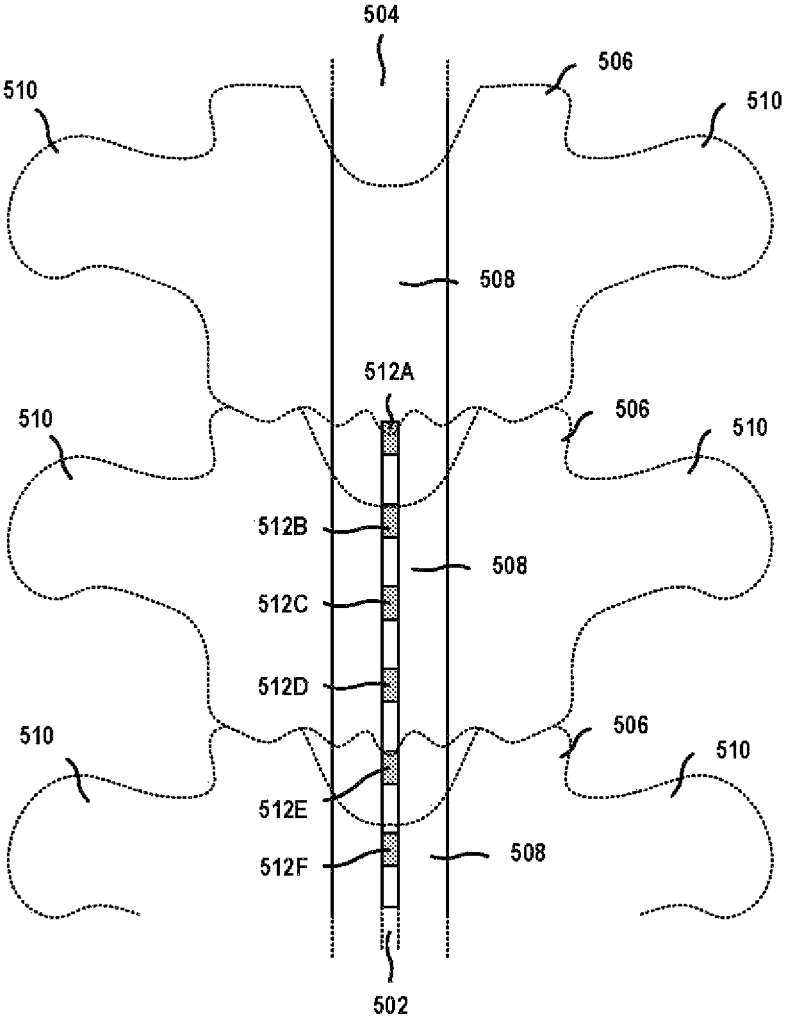
FIG. 9 illustrates an example lead implanted adjacent to a spinal cord, in accordance with one or more techniques of this disclosure.

FIG. 9 illustrates example lead 502 of an implantable medical device (e.g., IMD 110) implanted adjacent to a spinal cord 504 in an epidural space, in accordance with one or more techniques of this disclosure. Lead 502 may be an example of leads 130 of FIG. 1. FIG. 9 illustrates vertebrae 506 with lamina 508 and transverse processes 510. For simplicity of illustration, FIG. 9 does not depict the spinous processes. In the illustrated example, lead 502 includes electrodes 512A-512F (collectively "electrodes 512"). FIG. 9 illustrates lead 502 in the location along spinal cord 504 at which lead 502 is implanted (e.g., the "implant location"). IMD 110 is programmed with one or more sets of therapy parameters (e.g., amplitude and pulse width, etc.) to provide effective therapy to patient 105 at the implant location.

Figure 10:
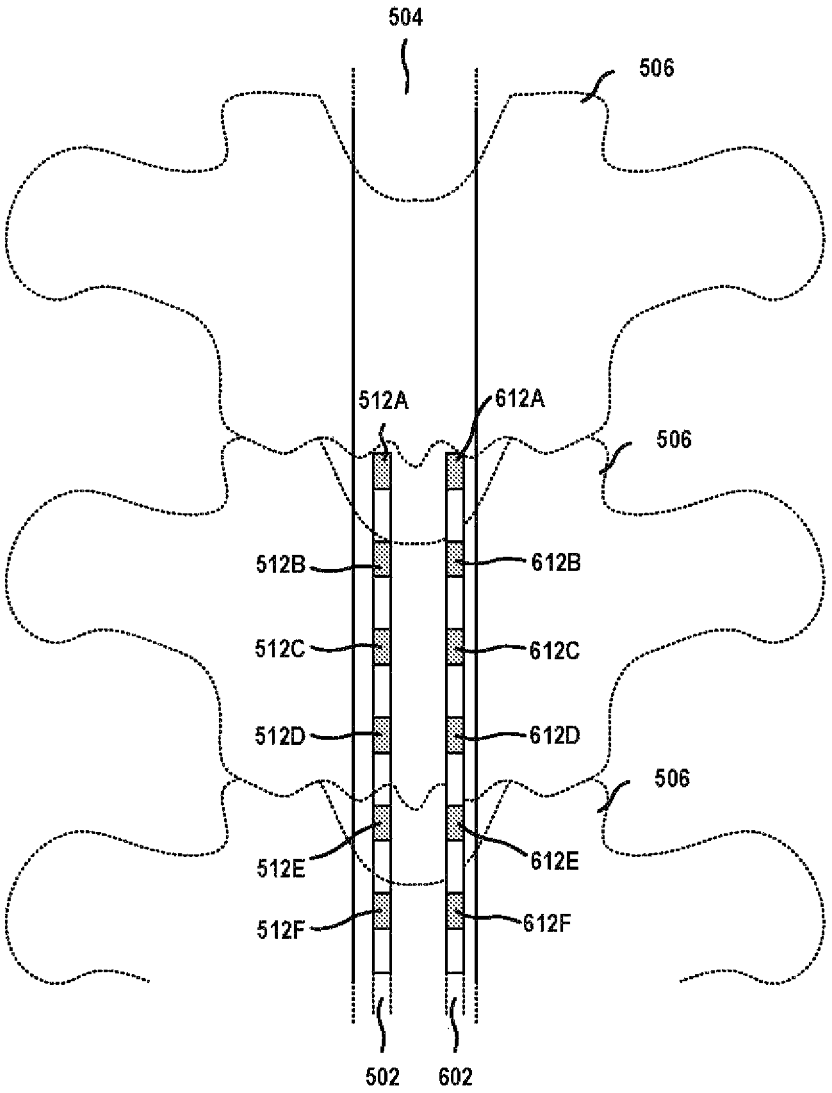
FIG. 10 illustrates example leads implanted adjacent to a spinal cord, in accordance with one or more techniques of this disclosure.

FIG. 10 illustrates multiple leads 502 and 602 of IMD 110 implanted adjacent to spinal cord 504 in an epidural space, in accordance with one or more techniques of this disclosure. Leads 502 and 602 may be an example of leads 130 of FIG. 1. Stimulus may be delivered on electrodes 512A and 512B of lead 502 and 612A and 612B of lead 602. The ECAP and/or LFP may be sensed on electrodes 512E and 512F of lead 502 and 612E and 612F of lead 602. FIG. 10 illustrates leads 502 and 602 at the implanted location.

Figure 11:
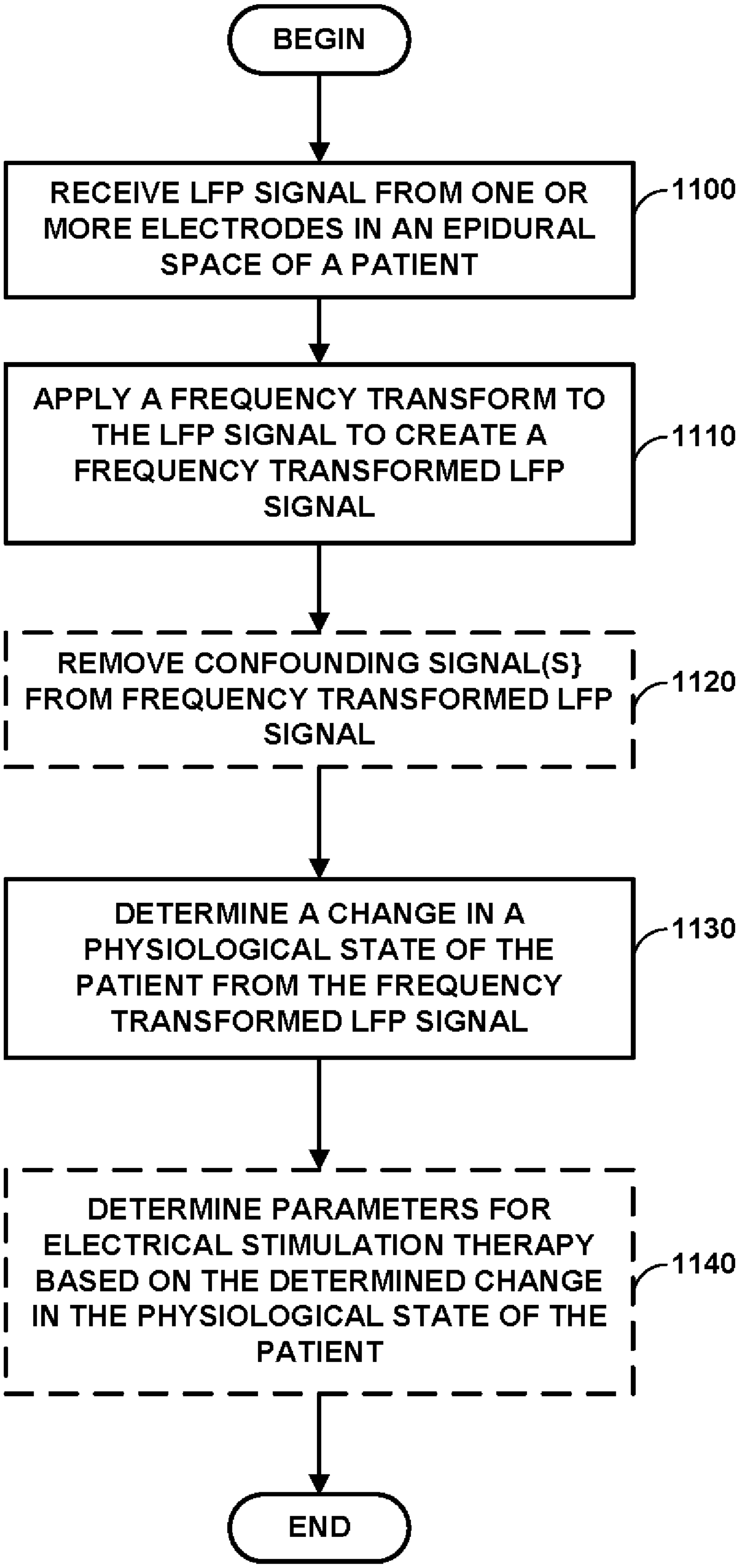
FIG. 11 is a flowchart illustrating an example technique of the disclosure.

FIG. 11 is a flowchart illustrating an example technique of the disclosure. The techniques of FIG. 11 may be performed by processing circuitry described above, including IMD 110 (FIG. 1), external programmer 150 (FIG. 1), processing circuitry 210 (FIG. 2), processing circuitry 352 (FIG. 3), and/or processing circuitry 410 (FIG. 4). That is, the techniques of FIG. 11 may be performed by an IMD, an external programmer, another external device, or any combination thereof. Processing circuitry 210 will be described herein as an example.

In one example, processing circuitry 210 may be configured to receive an LFP signal from one or more electrodes in an epidural space of a patient (1100). The leads (including one or more electrodes) connected to the sensing circuitry may be arranged in any of the placements described above. In one example, one or more electrodes positioned on or near a DRG. Processing circuitry 210 may be further configured to apply a frequency transform to the LFP signal to create a frequency transformed LFP signal (1110). In one example, the frequency transform is a wavelet transform. In one optional example of the disclosure, processing circuitry 210 may remove confounding signal(s) from the frequency transformed LFP signal (1120). Examples of confounding signals may include a stimulation signal, an ECG, and/or ECAPs signals.

Processing circuitry 210 may determine a change in a physiological state of the patient from the frequency transformed LFP signal (1130). The determination of a change in the physiological state (e.g., including a pain state) may be based on one or more measurements of power in the frequency transformed LFP signal over one or more spectral bands, as described above. Optionally, processing circuitry 210 may further determine parameters for electrical stimulation therapy based on the determined change in the physiological state (e.g., including a pain state) of the patient (1140).

Example systems, devices, and techniques of the disclosure are described below.

Example 1—A system comprising: a memory configured to receive and store a local field potential (LFP) signal received from one or more electrodes in an epidural space of a patient; and processing circuitry configured to: apply a frequency transform to the LFP signal to create a frequency transformed LFP signal; and determine a change in a physiological state of the patient from the frequency transformed LFP signal.

Example 2—The system of Example 1, wherein to determine the change in the physiological state of the patient, the processing circuitry is further configured to: measure a power of the frequency transformed LFP signal in one or more spectral bands; and determine the change in the physiological state of the patient based on the measured power.

Example 3—The system of Example 2, wherein to measure the power of the frequency transformed LFP signal in one or more spectral bands, the processing circuitry is further configured to: measure the power of the frequency transform LFP signal in one or more spectral bands below 200 Hz.

Example 4—The system of Example 2, wherein to measure the power of the frequency transformed LFP signal in one or more spectral bands, the processing circuitry is further configured to: measure the power of the frequency transform LFP signal in one or more spectral bands below 80 Hz.

Example 5—The system of any of Examples 2-4, wherein to measure the power of the frequency transformed LFP signal in one or more spectral bands, the processing circuitry is further configured to: measure the power of the frequency transform LFP signal in one or more spectral bands over a period of time.

Example 6—The system of any of Examples 2-5, wherein to determine the change in the physiological state of the patient, the processing circuitry is further configured to: determine the change in the physiological state of the patient based on the measured power and one or more of an evoked compound action potentials (ECAPs) signal, an output of an accelerometer, a respiration measure, or an electrocardiogram (ECG) signal.

Example 7—The system of Example 1, wherein to determine the change in the physiological state of the patient, the processing circuitry is further configured to: compare respective powers of the frequency transformed LFP signal in two or more spectral bands; and determine the change in the physiological state of the patient based on the comparison.

Example 8—The system of any of Examples 1-7, wherein the physiological state of the patient includes one or more of a degree or extent of pain, a degree of sensitivity to pain, a susceptibility of a neural target to transmit or receive information, a susceptibility of a neural target to respond therapeutically to electrical stimulation, or a biochemical state.

Example 9—The system of any of Examples 1-8, wherein the processing circuitry is further configured to: determine one or more parameters for electrical stimulation therapy based on the determined change in the physiological state of the patient.

Example 10—The system of any of Examples 1-9, wherein to apply the frequency transform to the LFP signal to create the frequency transformed LFP signal, the processing circuitry is configured to: apply a wavelet transform to the LFP signal to create the frequency transformed LFP signal.

Example 11—The system of any of Examples 1-10, wherein the processing circuitry is further configured to: remove a confounding signal from the frequency transformed LFP signal.

Example 12—The system of Example 11, wherein the confounding signal is an electrocardiogram (ECG) signal.

Example 13—The system of Example 12, wherein to remove the ECG signal from the frequency transformed LFP signal, the processing circuitry is further configured to: identify peaks in the ECG signal; and subtract the ECG peaks from the frequency transformed LFP signal.

Example 14—The system of Example 11, wherein the confounding signal is one or more of an electrocardiogram (ECG) signal, a stimulation signal, or an evoked compound action potentials (ECAPs) signal.

Example 15—The system of any of Examples 1-14, wherein the processing circuitry is further configured to: initiate a measurement of the LFP signal when the patient is in a supine position.

Example 16—The system of Example 15, wherein to initiate the measurement of the LFP signal, the processing circuitry is further configured to: initiate the measurement of the LFP signal in response to an accelerometer detection of the supine position.

Example 17—The system of Example 15, wherein to initiate the measurement of the LFP signal, the processing circuitry is further configured to: initiate the measurement of the LFP signal in response to a detection of a constant evoked compound action potentials (ECAPs) signal.

Example 18—The system of Example 15, wherein the processing circuitry is further configured to: switch an electrical stimulation therapy to active discharge when initiating the measurement of the LFP signal.

Example 19—The system of Example 15, wherein to initiate the measurement of the LFP signal, the processing circuitry is further configured to: initiate the measurement of the LFP signal in response to an off phase of a duty cycle of an electrical stimulation therapy.

Example 20—The system of any of Examples 1-19, further comprising the one or more electrodes.

Example 21—The system of Example 20, wherein the one or more electrodes include one or more macro-electrodes.

Example 22—The system of Example 20, wherein the one or more electrodes are arranged in a wide bi-pole configuration.

Example 23—The system of Example 20, wherein the one or more electrodes include laterally placed leads from mid-line of a spine of the patient.

Example 24—The system of Example 20, wherein the one or more electrodes are placed on a dorsal root ganglion (DRG).

Example 25—The system of Example 20, wherein the one or more electrodes are positioned on two leads arranged head to tail.

Example 26—The system of any of Examples 1-24, wherein the processing circuitry is part of an implantable medical device (IMD), wherein the IMD is implanted in the patient.

Example 27—The system of any of Examples 1-24, wherein the processing circuitry is part of a patient programmer that is external to the patient.

Example 28—A method comprising: receiving, by processing circuitry, a local field potential (LFP) signal received from one or more electrodes in an epidural space of a patient; applying, by the processing circuitry, a frequency transform to the LFP signal to create a frequency transformed LFP signal; and determining, by the processing circuitry, a change in a physiological state of the patient from the frequency transformed LFP signal.

Example 29—The method of Example 28, wherein determining the change in the physiological state of the patient comprises: measuring a power of the frequency transformed LFP signal in one or more spectral bands; and determining the change in the physiological state of the patient based on the measured power.

Example 30—The method of Example 29, wherein measuring the power of the frequency transformed LFP signal in one or more spectral band comprises: measuring the power of the frequency transform LFP signal in one or more spectral bands below 200 Hz.

Example 31—The method of Example 29, wherein measuring the power of the frequency transformed LFP signal in one or more spectral bands comprises: measuring the power of the frequency transform LFP signal in one or more spectral bands below 80 Hz.

Example 32—The method of any of Examples 29-31, wherein measuring the power of the frequency transformed LFP signal in one or more spectral bands comprises: measuring the power of the frequency transform LFP signal in one or more spectral bands over a period of time.

Example 33—The method of any of Examples 29-32, wherein determining the change in the physiological state of the patient comprises: determining the change in the physiological state of the patient based on the measured power and one or more of an evoked compound action potentials (ECAPs) signal, an output of an accelerometer, a respiration measure, or an electrocardiogram (ECG) signal.

Example 34—The method of Example 28, wherein determining the change in the physiological state of the patient comprises: comparing respective powers of the frequency transformed LFP signal in two or more spectral bands; and determining the change in the physiological state of the patient based on the comparison.

Example 35—The method of any of Examples 28-34, wherein the physiological state of the patient includes one or more of a degree or extent of pain, a degree of sensitivity to pain, a susceptibility of a neural target to transmit or receive information, a susceptibility of a neural target to respond therapeutically to electrical stimulation, or a biochemical state.

Example 36—The method of any of Examples 28-35, the method further comprising: determining one or more parameters for electrical stimulation therapy based on the determined change in the physiological state of the patient.

Example 37—The method of any of Examples 28-36, wherein applying the frequency transform to the LFP signal to create the frequency transformed LFP signal comprises: applying a wavelet transform to the LFP signal to create the frequency transformed LFP signal.

Example 38—The method of any of Examples 28-37, the method further comprising: removing a confounding signal from the frequency transformed LFP signal.

Example 39—The method of Example 28, wherein the confounding signal is an electrocardiogram (ECG) signal.

Example 40—The method of Example 39, wherein removing the ECG signal from the frequency transformed LFP signal comprises: identifying peaks in the ECG signal; and subtracting the ECG peaks from the frequency transformed LFP signal.

Example 41—The method of Example 38, wherein the confounding signal is one or more of an electrocardiogram (ECG) signal, a stimulation signal, or an evoked compound action potentials (ECAPs) signal.

Example 42—The method of any of Examples 28-41, the method further comprising: initiating a measurement of the LFP signal when the patient is in a supine position.

Example 43—The method of Example 42, wherein initiating the measurement of the LFP signal comprises: initiating the measurement of the LFP signal in response to an accelerometer detection of the supine position.

Example 44—The method of Example 42, wherein initiating the measurement of the LFP signal comprises: initiating the measurement of the LFP signal in response to a detection of a constant evoked compound action potentials (ECAPs) signal.

Example 45—The method of Example 42, the method further comprising: switching an electrical stimulation therapy to active discharge when initiating the measurement of the LFP signal.

Example 46—The method of Example 42, wherein initiating the measurement of the LFP signal comprises: initiating the measurement of the LFP signal in response to an off phase of a duty cycle of an electrical stimulation therapy.

Example 47—The method of Example 28, wherein the one or more electrodes include one or more macro-electrodes.

Example 48—The method of Example 28, wherein the one or more electrodes are arranged in a wide bi-pole configuration.

Example 49—The method of Example 28, wherein the one or more electrodes include laterally placed leads from mid-line of a spine of the patient.

Example 50—The method of Example 28, wherein the one or more electrodes are placed on a dorsal root ganglion (DRG).

Example 51—The method of Example 28, wherein the one or more electrodes are positioned on two leads arranged head to tail.

Example 52—The method of any of Examples 28-51, wherein the method is performed by processing circuitry that is part of an implantable medical device (IMD), wherein the IMD is implanted in the patient.

Example 53—The method of any of Examples 28-51, wherein the method is performed by processing circuitry that is part of a patient programmer that is external to the patient.

Example 54—A non-transitory computer-readable medium storing instructions that, when executed, causes one or more processors to perform the methods of any of Examples 28-53.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:

a memory configured to receive and store a local field potential (LFP) signal received from one or more electrodes disposed in an epidural space adjacent at least one of a cervical, thoracic, or lumbar region of a spinal cord of a patient; and processing circuitry configured to:

determine that an evoked compound action potential (ECAP) signal fluctuates less than a threshold amount during a period of time;

obtain the LFP signal sensed during the period of time;

apply a frequency transform to the LFP signal to create a frequency transformed LFP signal; and determine a change in a physiological state of the patient from the frequency transformed LFP signal.

2. The system of claim 1, wherein to determine the change in the physiological state of the patient, the processing circuitry is further configured to:

measure a power of the frequency transformed LFP signal in one or more spectral bands; and determine the change in the physiological state of the patient based on the measured power.

3. The system of claim 2, wherein the ECAP signal is a first ECAP signal, and wherein to determine the change in the physiological state of the patient, the processing circuitry is further configured to:

determine the change in the physiological state of the patient based on the measured power and one or more of a second ECAP signal, an output of an accelerometer, a respiration measure, or an electrocardiogram (ECG) signal.

4. The system of claim 1, wherein to determine the change in the physiological state of the patient, the processing circuitry is further configured to:

compare respective powers of the frequency transformed LFP signal in two or more spectral bands; and determine the change in the physiological state of the patient based on the comparison.

5. The system of claim 1, wherein the physiological state of the patient includes one or more of a degree or extent of pain, a degree of sensitivity to pain, a susceptibility of a neural target to transmit or receive information, a susceptibility of a neural target to respond therapeutically to electrical stimulation, or a biochemical state.

6. The system of claim 1, wherein the processing circuitry is further configured to:

determine one or more parameters for electrical stimulation therapy based on the determined change in the physiological state of the patient.

7. The system of claim 1, wherein to apply the frequency transform to the LFP signal to create the frequency transformed LFP signal, the processing circuitry is configured to:

apply a wavelet transform to the LFP signal to create the frequency transformed LFP signal.

8. The system of claim 1, wherein the processing circuitry is further configured to:

remove a confounding signal from the frequency transformed LFP signal.

9. The system of claim 8, wherein the confounding signal is one or more of an electrocardiogram (ECG) signal, a stimulation signal, or an evoked compound action potential (ECAP) signal.

10. The system of claim 9, wherein to remove the ECG signal from the frequency transformed LFP signal, the processing circuitry is further configured to:

identify peaks in the ECG signal; and subtract the ECG peaks from the frequency transformed LFP signal.

11. The system of claim 1, wherein the processing circuitry is further configured to:

initiate a measurement of the LFP signal when the patient is in a supine position.

12. The system of claim 1, further comprising the one or more electrodes, and wherein the one or more electrodes are disposed within the epidural space to sense the LFP signal from a dorsal root ganglion (DRG).

13. The system of claim 1, wherein the processing circuitry is part of an implantable medical device (IMD), wherein the IMD is configured to be implanted in the patient.

14. The system of claim 1, wherein the processing circuitry is configured to adjust, based on the change to the physiological state of the patient, a value of a stimulation parameter that defines electrical stimulation therapy, and wherein the system further comprises stimulation circuitry configured to generate, based on the value of the stimulation parameter, the electrical stimulation therapy deliverable to the spinal cord of the patient.

15. The system of claim 1, wherein the LFP signal is received from the one or more electrodes disposed in the epidural space adjacent at least one of dorsal root ganglion, a dorsal root, a dorsal rootlet, a dorsal root entry zone, a ventral root, or a ventral rootlet, and wherein the cervical, thoracic, or lumbar region of the spinal cord includes one or more of the dorsal root, the dorsal rootlet, the dorsal root entry zone, the ventral root, or the ventral rootlet.

16. A method comprising:

determining, by processing circuitry, that an evoked compound action potential (ECAP) signal fluctuates less than a threshold amount during a period of time;

obtaining, by the processing circuitry, a local field potential (LFP) signal sensed during the period of time, wherein the LFP signal is received from one or more electrodes disposed in an epidural space adjacent at least one of a cervical, thoracic, or lumbar region of a spinal cord of a patient;

applying, by the processing circuitry, a frequency transform to the LFP signal to create a frequency transformed LFP signal; and determining, by the processing circuitry, a change in a physiological state of the patient from the frequency transformed LFP signal.

17. The method of claim 16, wherein determining the change in the physiological state of the patient comprises:

measuring a power of the frequency transformed LFP signal in one or more spectral bands; and determining the change in the physiological state of the patient based on the measured power.

18. The method of claim 16, wherein determining the change in the physiological state of the patient comprises:

comparing respective powers of the frequency transformed LFP signal in two or more spectral bands; and determining the change in the physiological state of the patient based on the comparison.

19. The method of claim 16, wherein the physiological state of the patient includes one or more of a degree or extent of pain, a degree of sensitivity to pain, a susceptibility of a neural target to transmit or receive information, a susceptibility of a neural target to respond therapeutically to electrical stimulation, or a biochemical state.

20. The method of claim 16, further comprising:

determining one or more parameters for electrical stimulation therapy based on the determined change in the physiological state of the patient; and controlling stimulation circuitry to deliver the electrical stimulation therapy according to the one or more parameters.

21. A non-transitory computer-readable medium storing instructions that, when executed, causes one or more processors to:

determine that an evoked compound action potential (ECAP) signal fluctuates less than a threshold amount during a period of time;

obtain a local field potential (LFP) signal sensed during the period of time, wherein the LFP signal is received from one or more electrodes disposed in an epidural space adjacent at least one of a cervical, thoracic, or lumbar region of a spinal cord of a patient;

apply a frequency transform to the LFP signal to create a frequency transformed LFP signal; and determine a change in a physiological state of the patient from the frequency transformed LFP signal.

* * * * *